United States Patent
Ishikawa et al.

(10) Patent No.: US 8,059,000 B2
(45) Date of Patent: *Nov. 15, 2011

(54) WEARABLE/PORTABLE PROTECTION FOR A BODY

(75) Inventors: Muriel Y. Ishikawa, Livermore, CA (US); Edward K. Y. Jung, Bellevue, WA (US); Cameron A. Myhrvold, Bellevue, WA (US); Conor L. Myhrvold, Bellevue, WA (US); Nathan P. Myhrvold, Bellevue, WA (US); Lowell L. Wood, Jr., Bellevue, WA (US); Victoria Y. H. Wood, Livermore, CA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/454,180

(22) Filed: May 12, 2009

(65) Prior Publication Data

US 2010/0004567 A1     Jan. 7, 2010

Related U.S. Application Data

(63) Continuation-in-part of application No. 11/136,339, filed on May 24, 2005, now Pat. No. 7,548,168.

(51) Int. Cl.
   *G08B 23/00*     (2006.01)
(52) U.S. Cl. .............. 340/573.1; 340/689; 280/730.1; 2/455; 2/465
(58) Field of Classification Search .......... 340/573.1, 340/539.1, 689, 573.6; 280/730.1, 734, 735; 2/455, 465, 468, DIG. 3
See application file for complete search history.

(56) References Cited

U.S. PATENT DOCUMENTS

| | | |
|---|---|---|
| 3,398,406 A | 8/1968 | Waterbury |
| 3,889,970 A | 6/1975 | Astheimer et al. |
| 3,960,386 A | 6/1976 | Wallsten |
| 4,287,250 A | 9/1981 | Rudy |
| 4,817,902 A | 4/1989 | Mason |
| 4,825,625 A | 5/1989 | Hufford |
| 4,875,548 A | 10/1989 | Lorsbach |
| 4,977,623 A | 12/1990 | DeMarco |
| 5,005,240 A | 4/1991 | Vrzalik |
| 5,052,065 A | 10/1991 | West |
| 5,054,811 A | 10/1991 | Unterforsthuber et al. |
| 5,150,767 A | 9/1992 | Miller |
| 5,181,697 A | 1/1993 | Rumer |
| 5,202,831 A | 4/1993 | Blackburn et al. |
| 5,203,427 A | 4/1993 | Williams, Sr. et al. |
| 5,299,397 A | 4/1994 | Ahern |
| 5,308,113 A | 5/1994 | Moriset |

(Continued)

FOREIGN PATENT DOCUMENTS

DE     195 41 998 A1     5/1997

(Continued)

OTHER PUBLICATIONS

U.S. Appl. No. 12/148,512, Hyde et al.

(Continued)

*Primary Examiner* — Anh V La

(57) ABSTRACT

In one embodiment, a particular state of a body is sensed. In response to the sensing, at least one action is taken to modulate a projected adverse interaction between the body or a portion thereof and at least one object in the environment of the body.

45 Claims, 19 Drawing Sheets

U.S. PATENT DOCUMENTS

| | | | |
|---|---|---|---|
| 5,362,098 | A | 11/1994 | Guill |
| 5,372,429 | A | 12/1994 | Beaver, Jr. et al. |
| 5,478,114 | A | 12/1995 | Maurer et al. |
| 5,592,705 | A | 1/1997 | West |
| 5,803,263 | A | 9/1998 | Pozzo |
| 5,810,385 | A | 9/1998 | Henseler et al. |
| 5,879,767 | A | 3/1999 | Matsushima et al. |
| 5,881,407 | A | 3/1999 | Chut Pt |
| 5,937,443 | A * | 8/1999 | Kageyama et al. ............. 2/69 |
| 5,945,912 | A | 8/1999 | Gulbrand |
| 5,960,494 | A | 10/1999 | Gilliland et al. |
| 6,125,478 | A | 10/2000 | Alaloof |
| 6,139,052 | A | 10/2000 | Preamprasitchai |
| 6,160,478 | A | 12/2000 | Jacobsen et al. |
| 6,181,998 | B1 | 1/2001 | Kanameda et al. |
| 6,219,605 | B1 | 4/2001 | Bauer et al. |
| 6,231,075 | B1 | 5/2001 | Otsu |
| 6,233,761 | B1 | 5/2001 | Neff |
| 6,314,596 | B1 | 11/2001 | Neff |
| 6,341,473 | B1 | 1/2002 | Kovacs et al. |
| 6,359,568 | B1 | 3/2002 | Johnson |
| 6,371,510 | B1 | 4/2002 | Marriott et al. |
| 6,382,660 | B1 | 5/2002 | Starner et al. |
| 6,396,427 | B1 | 5/2002 | Mattes et al. |
| 6,419,262 | B1 | 7/2002 | Fendt et al. |
| 6,447,006 | B1 | 9/2002 | Hess et al. |
| 6,594,835 | B2 | 7/2003 | West |
| 6,766,535 | B2 | 7/2004 | Duhamell et al. |
| 6,769,571 | B2 | 8/2004 | Mino |
| 6,792,342 | B2 | 9/2004 | Breed et al. |
| 6,848,708 | B2 | 2/2005 | Green et al. |
| 6,964,451 | B1 | 11/2005 | Bergey |
| 7,017,195 | B2 | 3/2006 | Buckman et al. |
| 7,018,495 | B2 | 3/2006 | Kannankeril et al. |
| 7,025,376 | B2 | 4/2006 | Dominissini |
| 7,032,924 | B2 | 4/2006 | Brewster et al. |
| 7,209,221 | B2 | 4/2007 | Breed et al. |
| 7,267,367 | B2 | 9/2007 | Barvosa-Carter et al. |
| 7,320,379 | B2 | 1/2008 | Gila et al. |
| 7,354,410 | B2 | 4/2008 | Perry et al. |
| 7,356,358 | B2 | 4/2008 | Sakai |
| 7,409,735 | B2 | 8/2008 | Kramer et al. |
| 7,444,698 | B2 | 11/2008 | Jackson, III |
| 7,481,453 | B2 | 1/2009 | Breed |
| 7,548,168 | B2 * | 6/2009 | Ishikawa et al. ........... 340/573.1 |
| 7,806,221 | B2 | 10/2010 | Mishra |
| 2001/0049840 | A1 * | 12/2001 | Atanasio ..................... 2/456 |
| 2002/0124882 | A1 | 9/2002 | Russo |
| 2002/0179390 | A1 | 12/2002 | Kitano et al. |
| 2003/0114972 | A1 | 6/2003 | Takafuji et al. |
| 2004/0049331 | A1 | 3/2004 | Schneider |
| 2005/0100251 | A1 | 5/2005 | Havens et al. |
| 2005/0154530 | A1 | 7/2005 | Hosokawa et al. |
| 2006/0131202 | A1 | 6/2006 | Kramer |
| 2006/0169753 | A1 | 8/2006 | Piucci et al. |
| 2007/0036947 | A1 | 2/2007 | Barwick |
| 2007/0182144 | A1 | 8/2007 | Aranzulla et al. |
| 2007/0205590 | A1 | 9/2007 | Klinkenberger et al. |
| 2008/0083640 | A1 | 4/2008 | Liu |
| 2008/0251332 | A1 | 10/2008 | Stuhmiller et al. |
| 2008/0307553 | A1 | 12/2008 | Jbeili et al. |
| 2010/0004819 | A1 | 1/2010 | Katz et al. |

FOREIGN PATENT DOCUMENTS

| | | |
|---|---|---|
| DE | 19631739 A1 | 2/1998 |
| JP | 2005-262994 A | 9/2005 |

OTHER PUBLICATIONS

U.S. Appl. No. 11/603,965, Hyde et al.

U.S. Appl. No. 11/868,416, filed Oct. 5, 2007, Hyde et al.

U.S. Appl. No. 11/726,706, filed Mar. 21, 2007, Hyde et al.

Davis, Ph.D., Warren; "What is a Tensor?"; located at www.physlink.com/Education/AskExperts/ae168.cfm; pp. 1-2; printed on Dec. 14, 2004.

Feliciano-Diaz, Xiomara "Geriatric Fall Hip Injury Prevention Device (Personal airbag system to prevent hip fractures on geriatrics)"; NSF Summer Undergraduate Fellowship in Sensor Technologies; located at www.ee.upenn.edu/~sunfest/pastProjects/Papers00/DiazXiomara.pdf, pp. 44-65.

"Frequently Asked Questions About Zylon and Body Armor, Written and Distributed by Toyobo Co., Ltd."; Osaka, Japan; 1996-2007; pp. 1-11.

Knight, Will; "Smart sports shoe adapts for optimal cushioning"; located at www.newscientist.com/news/print.jsp?id=ns99994969; bearing a date of May 6, 2004; pp. 1; printed on Dec. 7, 2004.

"Meta-Aramid Fiber"; (Jan. 25, 2008).

Nagourney, Eric; "Aging: Hip Protectors Don't Help Prevent Fractures in Falls"; The New York Times; bearing a date of Aug. 7, 2007; p. 1; The New York Times Company; printed on Aug. 9, 2007.

"Pro Fiber ZYLON®", Toyobo Co., Ltd.; Technical Information (Revised Sep. 2001); Osaka, Japan; bearing a date of Sep. 1, 2001; pp. 1-18.

S. Will; "Investigations by Mehler on the PBO-Fiber Zylon® from Toyobo"; Toyobo Co., Ltd. Mehler R&D, Osaka, Japan; bearing a date of May 7, 2002; pp. 1-5.

"Toyobo Material Safety Data Sheet", Toyobo Co., Ltd.; First issue: Aug. 10, 2000; Revised: Oct. 25, 2000; Material Safety Data Sheet No. F0374K; bearing a date of Oct. 25, 2000; pp. 1-3.

* cited by examiner

1400 SYSTEM
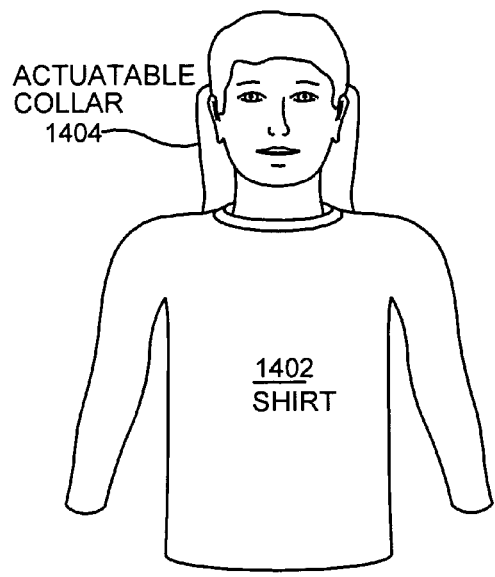
ACTUATABLE COLLAR 1404
1402 SHIRT
FIG. 14
1500 SYSTEM
1502 SHIRT
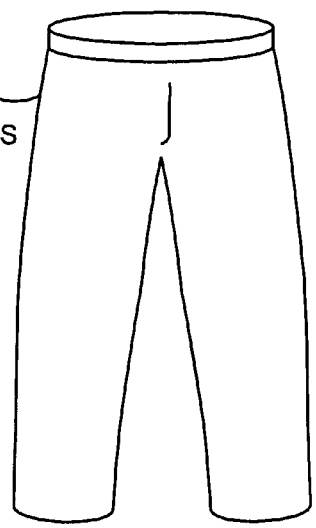
1504 TROUSERS
FIG. 15A
1550 JACKET
FIG. 15B

WEARABLE/PORTABLE PROTECTION FOR A BODY

RELATED APPLICATIONS

For purposes of the USPTO extra-statutory requirements, the present application constitutes a continuation-in-part of U.S. patent application Ser. No. 11/136,339, entitled WEARABLE/PORTABLE PROTECTION FOR A BODY, naming Muriel Y. Ishikawa, Edward K. Y. Jung; Cameron A. Myhrvold, Conor L. Myhrvold, Nathan P. Myhrvold, Lowell L. Wood, Jr., and Victoria Y. H. Wood as inventors, filed May 24, 2005, now U.S. Pat. No. 7,548,168, or is an application of which a currently co-pending application is entitled to the benefit of the filing date.

TECHNICAL FIELD

The present application relates to, in general, protecting one or more parts of a body.

SUMMARY

In one embodiment, a method includes but is not limited to sensing a particular state of a body. In response to the sensing, protecting the body from an object by at least determining one or more protective specifics related to at least one protective action based upon specifics of the state. Additionally, at least one protective action is activated that includes at least the one or more protective specifics based on the determining. In addition to the foregoing, other method aspects are described in the claims, drawings, and text forming a part of the present application.

In a different embodiment, a method includes but is not limited to placing at least a portion of a system at least in part on a break associated with a body. The system that is placed on the break includes at least (1) a sensor that is substantially capable of sensing at least a particular state of a body; and (2) a protective instrument sub-system that activates a protective mode in response to the sensor sensing the particular state. The protective instrument sub-system includes at least two individually activatable portions. The system is configured to have at least a portion of the protective instrument sub-system located at least in part on the body. In addition to the foregoing, other method/system aspects are described in the claims, drawings, and text forming a part of the present application.

In another embodiment, a system includes but is not limited to a detector that is substantially capable of detecting at least a particular state of a body, in which the system is substantially configured for having the detector positioned on the body. The system also may include circuitry for determining one or more specifics associated substantially with at least one protective action based substantially upon the state. Additionally, the system may include a protective instrument that is activated substantially based on the determination performed by the circuitry. The system may be configured for having the protective instrument placed substantially on the body. In addition to the foregoing, other system aspects are described in the claims, drawings, and text forming a part of the present application.

In another embodiment, the system includes but is not limited to a detector that is substantially capable of detecting at least a particular state of a body passing through a vicinity where the sensor is substantially located. The system also includes at least circuitry that determines whether to send an activation signal to a protective instrument located substantially at a body based on at least information derived from the detecting of the detector. The activation signal is appropriate for activating a protective instrument that is substantially protecting the body from the object. In addition to the foregoing, other system aspects are described in the claims, drawings, and text forming a part of the present application.

In another embodiment, a system includes but is not limited to circuitry that is substantially configured for receiving one or more signals from a detector, in which the one or more signals are associated substantially with at least a state of a body. Additionally, the circuitry is configured for determining whether to send at least one activation signal to a protective instrument located substantially at the body based on at least information derived from the one or more signals received. The at least one activation signal being appropriate for protecting the body from the object. In addition to the foregoing, other system aspects are described in the claims, drawings, and text forming a part of the present application.

In an embodiment, a system includes but is not limited to a machine-readable medium carrying one or more instructions for implementing a machine-implemented method. The method includes analyzing results of sensing a state of a body. The method also includes determining whether to activate a protective mode based substantially on the analyzing. Additionally, the method includes, based substantially on the analyzing, determining one or more specifics associated with the protective mode. In addition to the foregoing, other system/method aspects are described in the claims, drawings, and text forming a part of the present application.

In another embodiment, a system is provided that includes but is not limited to a sensor that is substantially capable of sensing at least a particular state of a body. Additionally, the system includes a protective instrument sub-system that activates a protective mode in response to the sensor sensing the particular state. The protective instrument sub-system includes at least two portions that are capable of being independently activated. The system is configured to have at least a portion of the protective instrument sub-system located at least in part on the body. In addition to the foregoing, other system aspects are described in the claims, drawings, and text forming a part of the present application.

In another embodiment, the system includes but is not limited to at least two sensors for sensing at least one acceleration of a body or portions thereof, at least one stored energy reservoir, and t least two actuators located on or about one or more parts of the body. The inflatable bags may be inflated as a result of t the at least one reservoir releasing a stored energy-medium to at least one actuator respectively. The system also includes at least one processor that determines if one or more consequences of a measured acceleration history are likely to result in an adverse interaction that will impose damage to the body as a result of interaction with at least one of the one or more objects. The processors also determine an amount and/or a release rate-vs.-time-program of the stored energy medium to release to each of a set of one or more of the at least two actuators. The amounts of stored energy-medium released and which actuators are selected to be within the set are determined according to a model of the body and a model of physical laws that determine a manner in which the body is expected to move relative to the one or more objects. The processor sends one or more signals to release the stored energy medium based on at least the determining of the amount and/or the release rate-vs.-time-program. In addition to the foregoing, other system aspects are described in the claims, drawings, and text forming a part of the present application.

In addition to the foregoing, various other method and/or system and/or program product aspects are set forth and described in the teachings such as text (e.g., claims and/or detailed description) and/or drawings of the present application.

The foregoing is a summary and thus contains, by necessity, simplifications, generalizations and omissions of detail; consequently, those skilled in the art will appreciate that the summary is illustrative only and is NOT intended to be in any way limiting. Other aspects, features, and advantages of the devices and/or processes and/or other subject matter described herein will become apparent in the teachings set forth herein.

BRIEF DESCRIPTION OF THE FIGURES

In the following, drawings, like reference numbers are sometimes used to refer to like elements. Although the following figures depict various examples of embodiments, the embodiments are not limited to the examples depicted in the figures.

FIG. 14 depicts a system that includes a shirt and collar for protecting parts of the body, within which any combination of systems of FIGS. 1-12A may be used.

FIG. 15A depicts a system that includes an example of a shirt and trousers for protecting parts of the body, within which any combination of systems of FIGS. 1-12A may be used.

FIG. 15B depicts an example of a jacket for protecting a body, within which any combination of systems of FIGS. 1-12A may be used.

DETAILED DESCRIPTION

Figure 1:
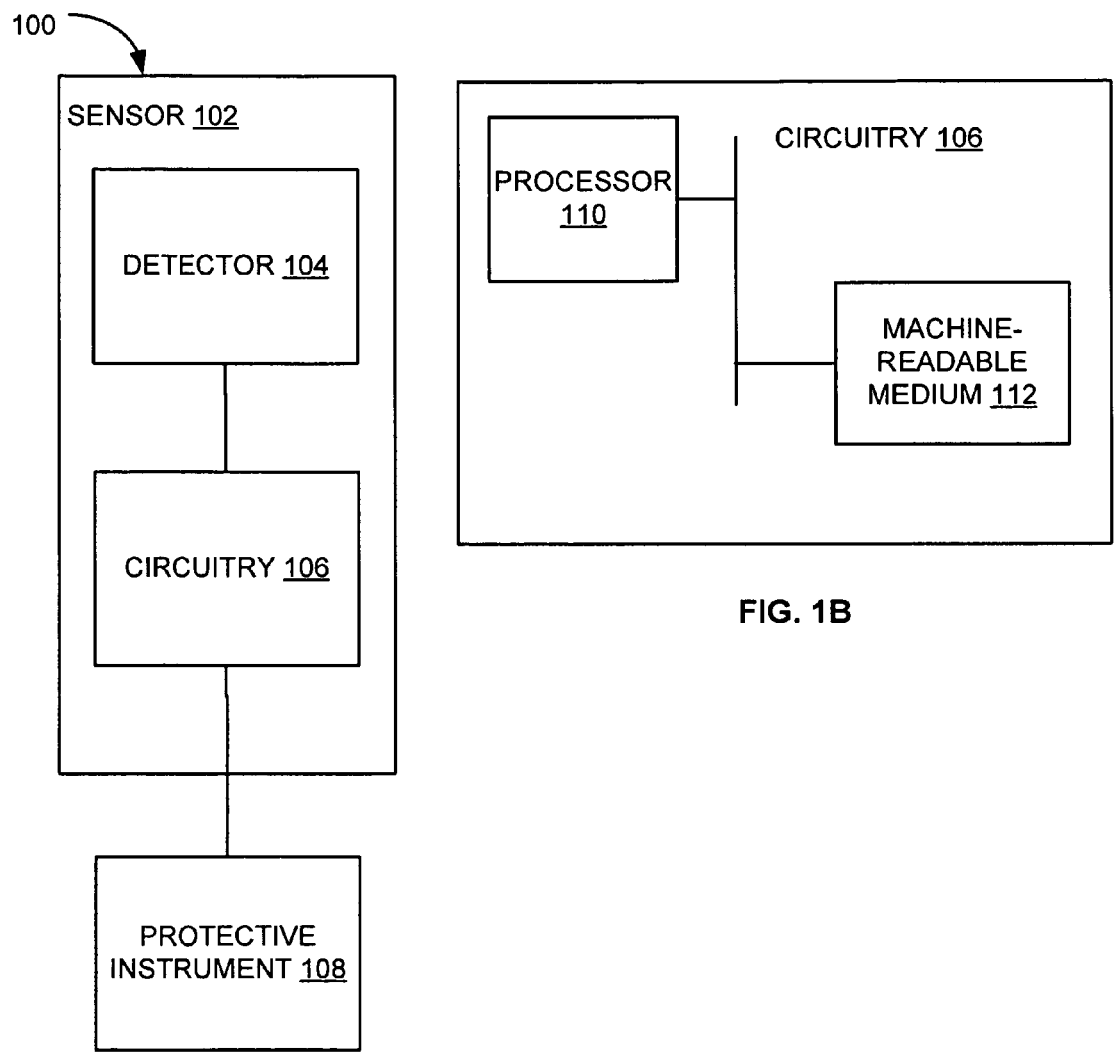
FIG. 1A depicts a block diagram of an embodiment of a system that provides protection to a body from adverse interactions with objects.
FIG. 1B depicts a block diagram of an embodiment of circuitry used in the system of FIG. 1A.

FIG. 1A depicts a block diagram of an embodiment of a system 100 that provides protection to a body from objects (e.g., a threat-object). System 100 includes sensor 102, which may include detector 104 and circuitry 106. System 100 also includes protective instrument 108. In alternative embodiments, system 100 may include other components in addition to and/or instead of those listed above.

System 100 may be used to protect a body from being damaged by adverse interaction with an object.

In an embodiment, system 100 is wearable, deployable body protection, which may be incorporated within, under, or as apparel. In this specification, the word "deploy" and its conjugations may be substituted for the word "activate" and its conjugations and adjectival and adverbial extensions and vice versa to obtain different embodiments as appropriate to context. System 100 may include one or more agents for diffusing momentum or impulse (or both) in space or in time (or both), similar in concept to the functioning of airbags in passenger automobiles. In an embodiment, system 100 may be worn by a locomotion-challenged person to cushion against prospective falls or collisions with environmental objects. In another embodiment, system 100 may be worn by athletes in lieu of traditional body-padding, helmets, and/or guards. In another embodiment, system 100 may be worn by people riding bicycles, skate-boarding, skating, skiing, snow-boarding, sledding and/or while engaged in various other sports or activities.

In an embodiment, system 100 lowers a peak dynamic stress on damage-vulnerable structural features of a body, such as a person, animal, or damage-vulnerable item. In an embodiment, system 100 may be included in a protective gear-set worn under, within, or as an integral feature of a garment. System 100 may control an acceleration and/or deceleration time-history of one or more body elements (e.g., acceleration and/or deceleration in conjunction with time and/or position histories) in the course of modulating what would otherwise be a damaging collision- or fall-event between the body and an object (e.g., a threat-object). In some embodiments, the time-history may be modulated by an inflation-mediated positioning of one or more flexible or inflatable or pressurized fluid-actuated elements. The time-history may modulate a timewise-brief-but-high peak amplitude acceleration 'program' into a time-integral-equivalent acceleration program that includes accelerations which are of a timewise-longer duration, but which have significantly smaller peak amplitudes than if the protective action not taken, so that associated peak mechanical stresses are proportionally reduced in their magnitudes and the likelihood of peak stress-induced damage substantially reduced. Alternatively or additionally, the acceleration may be diffused spatially, so that more of a body is accelerated more-or-less coherently from its exterior, rather than have accelerating forces transmitted throughout the body from a spatially-restricted set of body locations undergoing high peak accelerations and inducing correspondingly high peak mechanical stresses within the body.

Sensor 102 senses that a body, such as a person, animal, or other body, which is wearing or otherwise protected by system 100, is moving in a manner in which it is expected to come into contact with the object with potentially adverse consequences (e.g., at a too-high closing speed). In some embodiments, sensor 102 may be similar to the acceleration sensors included in airbag systems for passenger cars. For example, sensor 102 may have a range and range-rate sensing feature that determines when a potentially-adverse body-object contact is imminent and triggers a protective action (e.g., a cushioning action) to occur at-or-about the position and/or prior to a time at which the contact is expected to occur.

Detector 104 detects the motion of the body, either absolutely (e.g., via an accelerometer function) or relatively (referenced to objects in its vicinity), and sends signals including information about the motion and/or object for analysis to another part of sensor 102. In one embodiment, the detector 104 may detect an acceleration of low magnitude (i.e., significantly less than one gee vector acceleration) during a specified time-interval, which could be indicative of the body being in mid-fall (e.g., in near-free-fall). (In contrast, the sensor associated with a car airbag senses a high acceleration within a relatively short time-interval, corresponding to the abrupt slowing of a car during the initial phase of a crash incident). For example, detector 104 may include a silicon-based triaxial accelerometer for measuring acceleration (e.g., linear acceleration). Detector 104 may include a MicroElectroMechanical System (MEMS) accelerometer, which may, for instance, sense the displacement of a micro-cantilevered beam under acceleration transverse to its displacement-direction, e.g., by capacitive means. As a non-exclusive alternative, electrodes may be placed on a suitably-shaped and -mounted piezoelectric material for sensing a current and/or voltage generated by the piezoelectric material deforming in response to acceleration-induced stress. Some examples of materials that may be used in the piezoelectric version of detector 104 are lead zirconate titanate (PZT), lead zincate niobate (PZN), lead zincate niobate lead-titanate (PZN-PT), lead magnesium niobate lead-titanate (PMN-PT), lead lanthanum zirconate titanate (PLZT), Nb/Ta doped-PLZT, and barium zirconate titanate (BZT).

Detector 104 may include a range-detecting feature for detecting the distance between an object and the body, and may also include a range-rate feature for determining the rate at which this range is changing. Detector 104 may include means for estimating the direction and magnitude of one or more forces (e.g., gravity) that are accelerating the body or a portion thereof. Detector 104 may include a radar system and/or a sonar system. Detector 104 may include an angular acceleration or velocity detection feature in order to support estimation-in-advance of the location(s) on the body at which the object is likely to adversely interact. In another embodiment, other methods of detecting the (scalar or vector) acceleration, the fall-motion of a body, and/or of estimating the parameters of an impending adverse interaction may be used.

Circuitry 106 receives the signals from detector 104 and performs the analysis to determine whether there is a potentially harmful interaction in the foreseeable future. Circuitry 106 may analyze the signals from detector 104 to determine whether a particular state or condition-of-motion of the body has been detected. In an embodiment, the particular state or condition-of-motion may be associated with one-or-more objects in the vicinity of the body, a position, a motion, a change of motion, a velocity, an acceleration, and/or a direction of motion or a time-history of any of these, of the body or a portion thereof, either absolutely (referenced to the earth) or relative to one-or-more proximate objects. If an estimation is made by circuitry 106 that the state of condition-of-motion of the body is likely to result in an adverse interaction of above-threshold magnitude with one-or-more such objects, a signal is sent to cause one or more protective instruments 108 to implement a protective action. In an embodiment, the adverse interaction required to activate a protective action may be an expected level of pain or of physiological damage or of psychological damage imposed, or some combination of these. In an embodiment, the user can choose the expected type and/or degree of adverse interaction that suffices to activate a protective action. For example, circuitry 106 may analyze the signals sent from detector 104 to determine whether (1) an adverse interaction with an object is imminent and (2) whether the magnitude of that adverse interaction is above a threshold at which at least one protective action is required. If circuitry 106 estimates that an above-threshold adverse interaction is about to occur, a signal is sent to cause a protective instrument 108 to commence operation.

Similarly, circuitry 106 may determine one or more protective specifics (e.g., specifics related to how to protect the body most effectively). The protective specifics may relate to a manner of activating at least one protective action, to the sequencing of two or more protective actions, etc. The protective specifics may include at least two degrees of protection based on the current state of the body, in which each degree of protection is associated with a different location on the body or other body circumstance (e.g., estimated susceptibility-to-damage of one or another body-portion). In an embodiment, circuitry 106 may determine the degree to which at least one protective action is activated. For example, circuitry 106 may determine the extent to which an interfacing device is positioned, oriented or sized, and/or the amount or other quality of interfacing to be provided. After the protective specifics have been determined, instructions are sent, by circuitry 106, to activate the protective instrument 108 based on at least two extents and/or other protective specifics.

Circuitry 106 may make a selection from a range of different types or degrees of protective actions that can be implemented. For example, the range of protective actions may include adjusting the positions, orientations, natures, or degrees-of-actuation, or sizings of interfacing devices, and/or modifying an outer surface of an interfacing device to protect the body from a particular type of body-threatening object(s), e.g., a pointed, edged or high-temperature one. There may be a multiplicity of interfacing devices whose positions, orientations, shapes, sizes, surface characteristics, internal features, etc. can be adjusted, e.g., relative to each other, to various portions of the body or to the object(s). The position(s), degree(s) of cushioning provided, and/or the stiffnesses and/or hardness(es) of their outer surface(s) may be adjustable. Thus, circuitry 106 may be capable of selecting from a wide range of protective actions and the timing of and degree to which each of the several possible actions is activated. The selection of the protective action may be made by circuitry 106 estimating which protective action, or combination of protective actions, is most likely to ensure that a peak stress (e.g., a shear stress) imposed by the protectively-modulated adverse interaction with the object on at least one portion of the body is substantially less than some predetermined threshold for imposition of unacceptable damage.

The body positions at which to activate protective actions may be determined by circuitry 106 based on a detected (scalar or vector) direction or speed or acceleration of body motion (or motion of body parts or portions) relative to one-or-more objects that pose a threat of adverse interaction.

Circuitry 106 may include a false positive rejection circuit for determining whether an earlier determination that a condition eventuating in an adverse interaction between body and object is likely to occur is now false; in some implementations, heuristic techniques and/or additional signal processing are used to identify false positives (e.g., more accurately discriminate future adverse interaction from spurious movements and/or other physical, electromagnetic, and/or similar factors that may reduce/degrade detection). Circuitry 106 may include a manually and/or an automatically operated deactivation mechanism (e.g., a hardware/firmware/software switch and/or button) that deactivates the protective instrument 108, or some portion thereof; for example, an off switch/ button feature that a patient and/or interested party may use to deactivate the protective system and/or parts of it, in case of an erroneous deployment of the protective instrument. In an embodiment, the deactivation button may be used for resetting the system 100. The deactivation button may be used to deactivate system 100 (of a portion thereof) when system 100 has completed an interval of use. Alternatively, after using system 100, it could be discarded. Circuitry 106 may also include 'learning' features, so that it adapts to the usage patterns of an individual user, thereby providing protection ever more effectively adapted to the motions and object environment of a particular user.

Circuitry 106 may estimate appropriate protective actions to take based substantially on at least a model of a physical law that predicts at least one feature or manner in which the state of the body is expected to change with time, in at least one pertinent circumstance. The protective actions chosen may be expected to modulate a deceleration-vs.-time profile associated substantially with at least one part of the body. Circuitry 106 may include a feedback-aided control of the deceleration-vs.-time profile (which in some frames of reference might also be viewed as an acceleration profile, since both acceleration and deceleration can be viewed as quantities whose sign depends upon the frame of reference chosen), which feedback may be used to determine one or more additional or modulating protective actions to take. The feedback-enhanced control action may involve, after an initial protective action is taken, detector 104 measuring a subsequent state of the body. Based on that subsequent state, circuitry 106 may determine a new protective action and/or update the nature or degree of protective action already being taken.

The particular state may be associated substantially with at least a velocity or an acceleration of at least some portion of the body. The mechanical properties of the body may be estimated from a priori information (e.g., mass, dimensional and inertial moments information inputted to the circuitry 106 by the user or by user-supporting personnel) or may be estimated from at least one time-history of the motion of the body in the one-gee gravitational acceleration at/near the Earth's surface, or both. The determination of state is described herein, for sake of clarity, in relation to an acceleration (among other things). In some configurations, circuitry 106 may implement signal processing techniques including more robust factors in determining a condition likely to eventuate in an adverse body-object interaction. Such factors may include second order effects, and/or parameters defined by at least a portion of a body's position. Use of such factors may employ a variety of digital and/or analog techniques such as digital signal processing, tensor mathematics, and/or other techniques. In addition, those skilled in the art will appreciate that factors and/or techniques may be applied to other calculable components described herein, as appropriate to context.

Circuitry 106 may estimate at substantially any moment in time whether the body's likely trajectory will result in adverse interaction with one or more objects in the body's vicinity, e.g., impact upon a portion of the surface upon which the body is standing or walking. Circuitry 106 may determine whether body trajectory modulation required to avoid adverse interaction is substantially lacking, e.g., whether or not indicated deceleration is occurring. In other words, circuitry 106 may determine that the body's present trajectory is likely to result in an adverse interaction of at least one portion of it with at least one object, and the body or the pertinent portion thereof is not accelerating so as to likely avoid that interaction. As a result of this determination, circuitry 106 may send at least one signal to protective instrument 108 to initiate at least one protective action, and may thereafter monitor the consequences of the at least one action, possibly modulating its time-course as may be indicated to more optimally execute the at least one protective action.

In an embodiment, circuitry 106 may use the detection of an unusual motion-sequence (e.g., a transverse quasi-oscillation, growing in amplitude with time, of the upper body about the pelvis) as one of many indications that an adverse interaction (such as a fall and/or other uncontrolled motion toward a lower-located surface and/or a threat-object) may be commencing. Similarly, circuitry 106 may use detection of such an unusual motion-sequence followed by a time interval of significantly less than one-gee vector acceleration of a body portion as one of many indications that an adverse interaction is underway. In an embodiment, circuitry 106 is an analog circuit, while in another it is a digital circuit, while in yet another it is a hybrid of an analog and a digital circuit. Circuitry 106 is discussed further in conjunction with FIG. 1B.

Protective instrument 108 receives the signals from circuitry 106, causing protective instrument 108 to take a protective action. The protective action may be performed at, or substantially at or about, the body being protected. Protective instrument 108 may include a protective device useful for diffusing physical impulse in space, in time or in both, e.g., a device performing a padding or buffering or cushioning function. Once protective instrument 108 is activated (e.g., deployed), protective instrument 108 may form a protective device or structure that protects the body or at least one portion thereof. Protective instrument 108 may include a multiplicity of different devices or components that can be activated independently. Some non-exclusive examples of body portions where protective instrument 108 may be positioned or activated or deployed to in order to perform at least one protective function are the pelvis, neck, head, shoulders, torso, arms, legs, wrists, ankles, feet, hands, knees and elbows.

In one embodiment, the activated protective instrument 108 modulates the interaction of the body or at least one portion thereof with the at least one object in a significantly less adverse manner by spreading the interaction over a larger body portion or over a longer interval in time, or both, e.g., by means of a pad or cushion deployed so as to be between the at least one object and the at least one body-portion during at least a significant portion of the thereby-modulated interaction. This pad or cushion may be deployed from another location, or may be brought into effective being at the location of use, or its character significantly changed at time-of-use (e.g. its surface stiffened), or any combination of these.

The protective instrument sub-system 108 may be configured for being attached to a vulnerable structural feature associated at least with one portion of the body, and activating the protective instrument sub-system may act to lower a peak stress on a vulnerable structural feature associated with at least one portion of the body. Although only one sensor 102, detector 104, circuitry 106, and protective instrument 108 are shown, sensor 102 could be a multiplicity of the same or different sensors, detector 104 could be a multiplicity of the same or different detectors, instances of circuitry 106 could be a multiplicity of identical or distinct circuits, and protective instrument 108 could be a multiplicity of identical or different protective instruments.

FIG. 1B depicts a block diagram of an embodiment of circuitry 106. Circuitry 106 may include processor 110 and machine-readable medium 112. In alternative embodiments, circuitry 106 may include other components in addition to and/or instead of those listed above.

Processor 110 performs the analysis of the signals from detector 104, and determines whether the signals indicate a state that is estimated to result in an adverse interaction of at least one portion of the body with at least one object. For example, processor 110 may be used for estimating forward in time the trajectory of at least one portion of the body, based on the time history of its measured acceleration, perhaps supplemented by other information, either inferred or provided a priori, and comparing this with the known or estimated position and/or velocity of at least one object in the vicinity of the body or a portion thereof. Processor 110 may perform virtually any of the functions described above in connection with circuitry 106. Processor 110 may be an embedded microprocessor.

Machine-readable medium 112 (e.g., a computer-readable medium or other machine-readable medium) may store instructions that are implemented by processor 110. For example, machine-readable medium 112 may store software associated with a physical model for at least one portion of a body, including means for estimating its trajectory under various accelerations pertinent to adverse interactions with objects and the modulation thereof. As another example, machine-readable medium 112 may store instructions for carrying out virtually any of the other functions that circuitry 106 performs. Machine-readable medium 112 may include software that determines when to activate one or more portions or features of protective instrument 108. There may be multiple versions of the software stored on machine-readable medium 112, each version being specialized for different portions of the body. The different versions may be stored in the same machine-readable medium. In another embodiment, multiple aspects or features of protective instrument 108 are controlled by the same processor, which runs multiple versions or instantiations of the software to determine whether to activate and/or how to activate the protective instrument 108 features or aspects at different locations on or about the body.

Machine-readable medium 112 may also store information related to the specific features of the body and its portions that system 100 is protecting. Machine-readable medium 112 may store a computational model of a body and/or some of its portions that incorporates physical laws and/or engineering principles. Machine-readable medium 112 may include information related to approximations of the body's mass and inertial moments and/or its muscle and skeletal distribution and features. Machine-readable medium 112 may store at least some medical and/or damage- or vulnerability-related information about the body and/or at least one of its portions. In an embodiment, system 100 stores information related to a body's physical features, which may include information that is generic to large classes of bodies and/or may include specific information about the individual user, either provided a priori (such as by a user or a physician) or inferred by the system in the course of its operation. In one implementation, circuitry is utilized sufficient that information of machine-readable medium 112 can be replaced/modified as needed; for example, replaced/modified wirelessly and/or by an electronic device such as a plug-in module when upgrades/changes are available (e.g., model upgrades/changes and/or operating system upgrades/changes).

Figure 2:
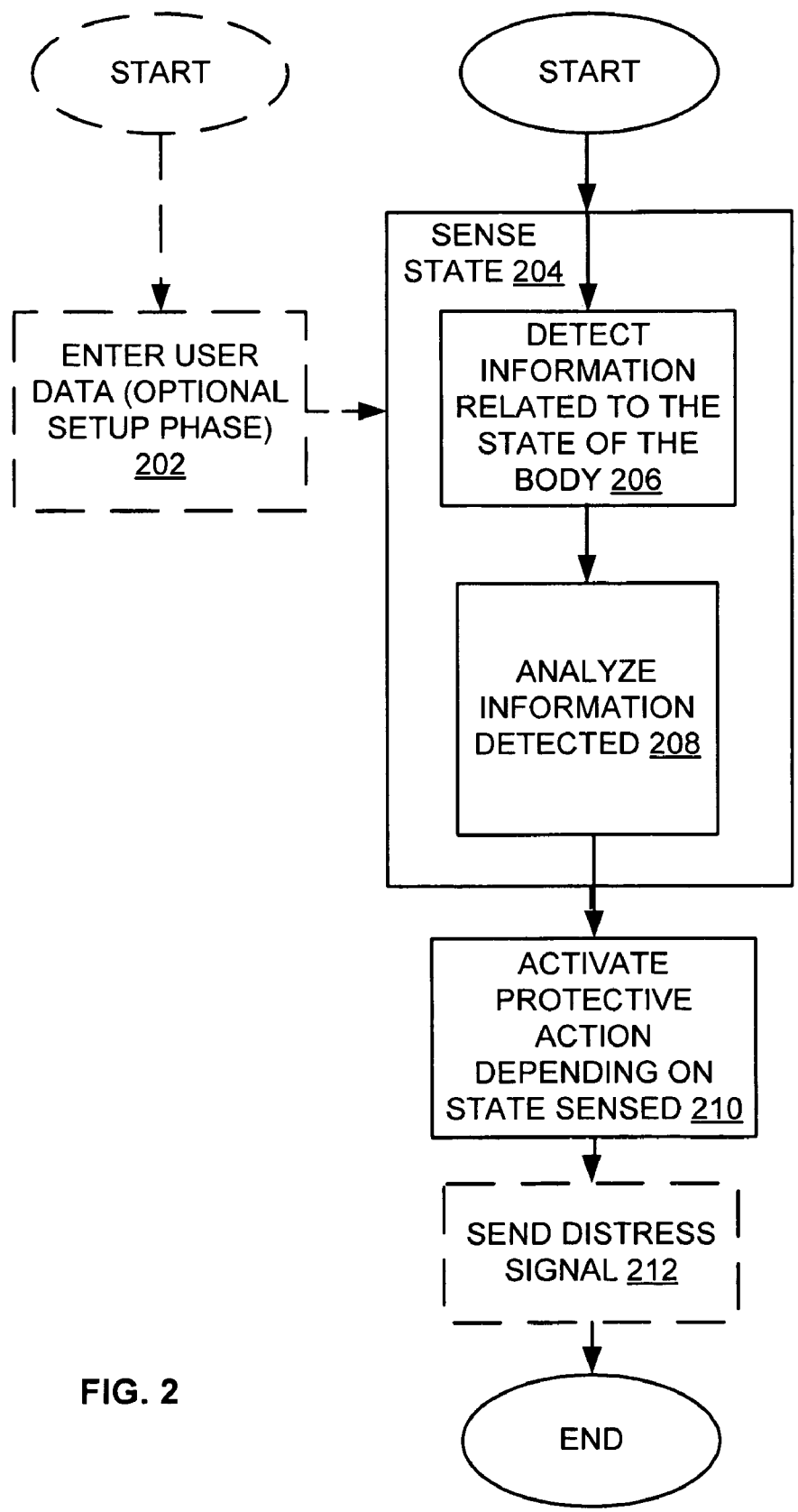
FIG. 2 depicts a flowchart of an example of a method that may be implemented by the system of FIG. 1A.

FIG. 2 depicts an example of a method 200, which may be implemented by system 100. In FIG. 2, dashed lines are used for the borders of boxes that correspond to steps that are optional. FIG. 2 includes an optional setup phase, step 202, during which user data are entered. The user data may include characteristics of the body being protected. For example, the characteristics may include body mass, inertial moments and dimensions, an identifier (such as a name), and/or a type (such as human, dog, cart, vehicle, or robot). During step 202, the user data may be stored within circuitry 106. In the embodiment of FIG. 1B, processor 110 may store the user data on machine-readable medium 112. During step 204, the state of the body, possibly including various portions thereof, is sensed by sensor 102 (FIG. 1A), and also may be recorded in machine-readable medium 112. Step 204 may include two sub-steps 206 and 208. During sub-step 206, detector 104 detects the state of the body, possibly including various portions thereof, and sends signals to circuitry 106 (FIG. 1A). During sub-step 208, circuitry 106 receives the signals from detector 104, and analyzes the signals, using information derived from machine-readable medium 112.

Sub-step 208 may involve circuitry 106 (FIG. 1A) analyzing the signals to estimate the motion of the body and/or various portions thereof and the body's current state, and may also involve estimation of its future-trajectory or the future trajectory of at least one portion thereof. Sub-step 208 may involve processor 110 (FIG. 1B) accessing and implementing instructions stored on machine-readable medium 112 (FIG. 1B). Sub-step 208 may also involve processor 110 accessing the user data entered during step 202 for use during the analysis. Depending on the results of the analysis, during sub-step 208, circuitry 106 sends signals to protective instrument 108. The information in these signals may be based upon the results of the analysis performed during sub-step 208, and may also be based on signals received from protective instrument 108. In another embodiment, no matter the results of the analysis, a signal is sent to protective instrument 108 (FIG. 1A), but the nature of the signal sent depends upon the state sensed. In yet another embodiment, protective instrument 108 may be activated by the lack of a signal being sent. Sub-step 208 is discussed further in conjunction with FIG. 3.

During step 210, depending on whether a signal was received from circuitry 106 or depending on the information in the signals sent from circuitry 106 (FIG. 1A), protective instrument 108 (FIG. 1A) is activated. During optional step 212, depending on the sensed state of the body and/or object, a distress signal may be sent. In an embodiment, the distress signal may be sent after a signal is received indicating that the body has undergone an adverse interaction with an object.

Figure 3:
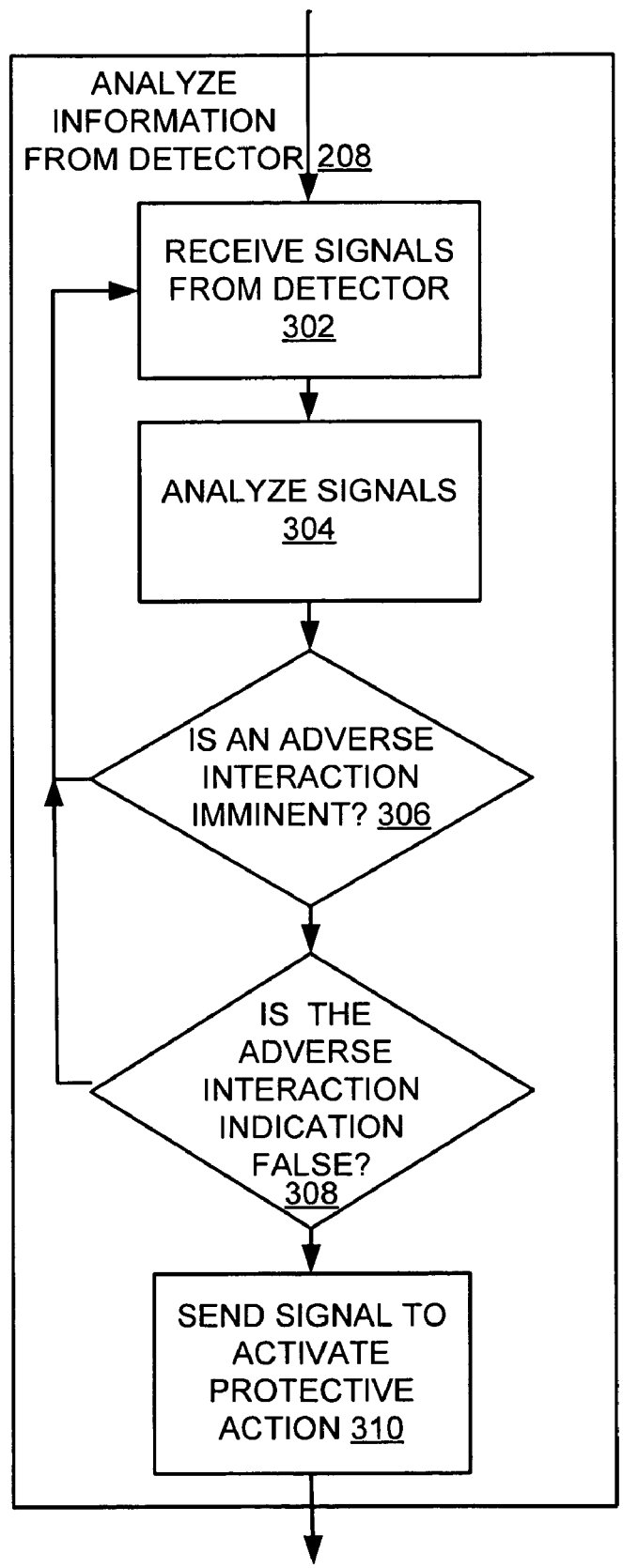
FIG. 3 depicts a flowchart of an example of a method that is an embodiment of a sub-step of the method of FIG. 2.

FIG. 3 depicts a flowchart of a method 300, which is an embodiment of sub-step 208 of FIG. 2. During sub-step 302, circuitry 106 receives signals from detector 104. During sub-step 304, the signals received are analyzed by circuitry 106 to estimate the state of the body and/or at least one of its portions, possibly using information stored in machine-readable medium 112. During sub-step 306, a decision is made, based on the estimated state of the body and/or at least one of its portions, as to whether the body and/or one of its portions is likely to undergo an adverse interaction with at least one object. If this adverse interaction is not estimated to occur with above-threshold likelihood, then method 300 returns to sub-step 302. If the adverse interaction is estimated to occur, then method 300 proceeds to sub-step 308.

At sub-step 308, a determination is made whether the expectation of the body undergoing an adverse interaction was a false positive. As discussed in conjunction with circuit 106 (FIG. 1A), a determination that there was a false positive may result from the body recovering from the state that it was in without the body actually commencing to undergo an adverse interaction. Alternatively, a false positive may be determined by performing a second more accurate calculational estimate of the immediate future to double-check the original estimate. One skilled in the art will recognize that signal processing and/or heuristic techniques can be applied to more accurately discriminate commencement of an adverse interaction from spurious movements or other physical, electromagnetic, or similar factors that may reduce/degrade detection. If sub-step 308 determines that the expectation of a future adverse interaction made by sub-step 306 is expected to be false, then method 300 returns to sub-step 302 to wait for the next signal from detector 104. Additionally, if protective instrument 108 (FIG. 1A) has been activated, circuit 106 may send one or more subsequent signals deactivating and/or otherwise inhibiting the protective action.

In an embodiment, step 308 is a machine-implemented step.

If sub-step 308 determines that the expectation of contact made by sub-step 306 is not expected to be false, then method 300 proceeds to step 310. During step 310, circuitry 106 sends signals to protective instrument 108, and may receive signals from 108. In other embodiments, the method 300 may include other sub-steps in addition to, and/or instead of, the steps listed above. Additionally, circuitry 106 (FIG. 1A) may perform the method 300 several times in response to different signals from detector 104 (FIG. 1A).

Figure 4:
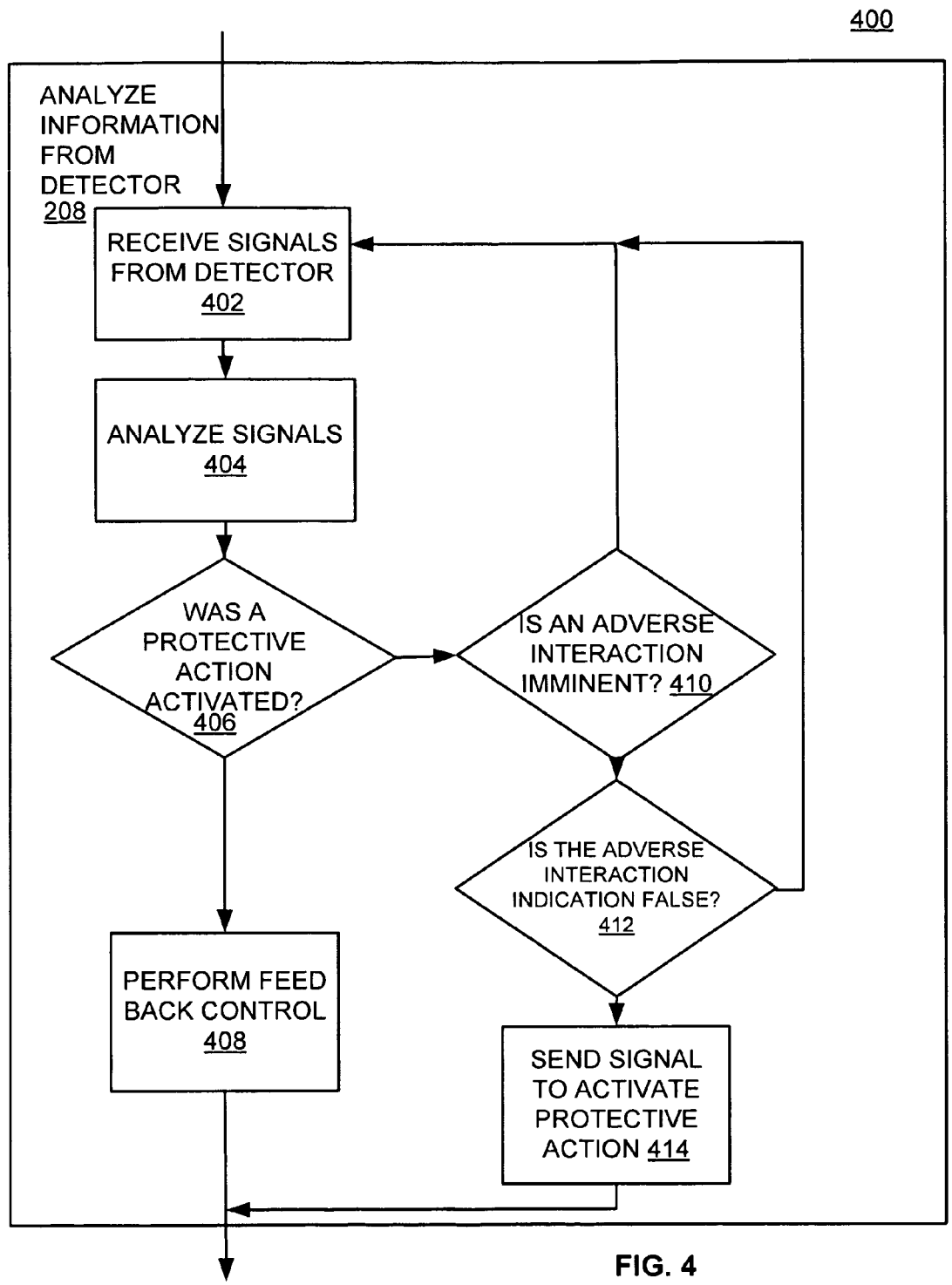
FIG. 4 depicts a flowchart of an example of a method that is another embodiment of the sub-step of the method of FIG. 2.

FIG. 4 depicts a flowchart of a method 400, which is another embodiment of sub-step 208 of FIG. 2. During sub-step 402, circuitry 106 receives signals from detector 104. During sub-step 404, circuitry 106 analyzes the signals received, including those that may be received from protective instrument(-set) 108. During sub-step 406, a determination is made whether the protective instrument(-set) was already activated. During sub-step 408, the analysis from sub-step 404 is used to adjust the control of the protective instrument. Sub-step 408 is discussed further in conjunction with FIG. 5.

Returning to sub-step 406, if it is determined that the protective instrument has not yet been activated, method 400 proceeds to step 410. During sub-step 410, a determination is made as to whether the body is likely to undergo an adverse interaction. If the body is not expected to undergo such an interaction, then method 400 returns to sub-step 402. If the body is expected to undergo such an interaction, then method 400 proceeds to sub-step 412. At sub-step 412, a determination is made whether the expectation of an adverse interaction is likely to be a false positive (e.g., via techniques described elsewhere herein). If sub-step 412 determines that the expectation of an adverse interaction made by sub-step 410 is expected to be false, then method 400 returns to sub-step 402 to wait for the next signal from detector 104 (FIG. 1A). If sub-step 412 determines that the expectation of an adverse interaction made by sub-step 410 is not expected to be false, then method 400 proceeds to step 414. During step 414, circuitry 106 (FIG. 1A) sends signals to activate protective instrument 108 (FIG. 1A). In other embodiments, method 400 may include other sub-steps in addition to, and/or instead of, the steps listed above. Additionally, circuitry 106 may perform the method 400 several times in response to different signals.

Figure 5:
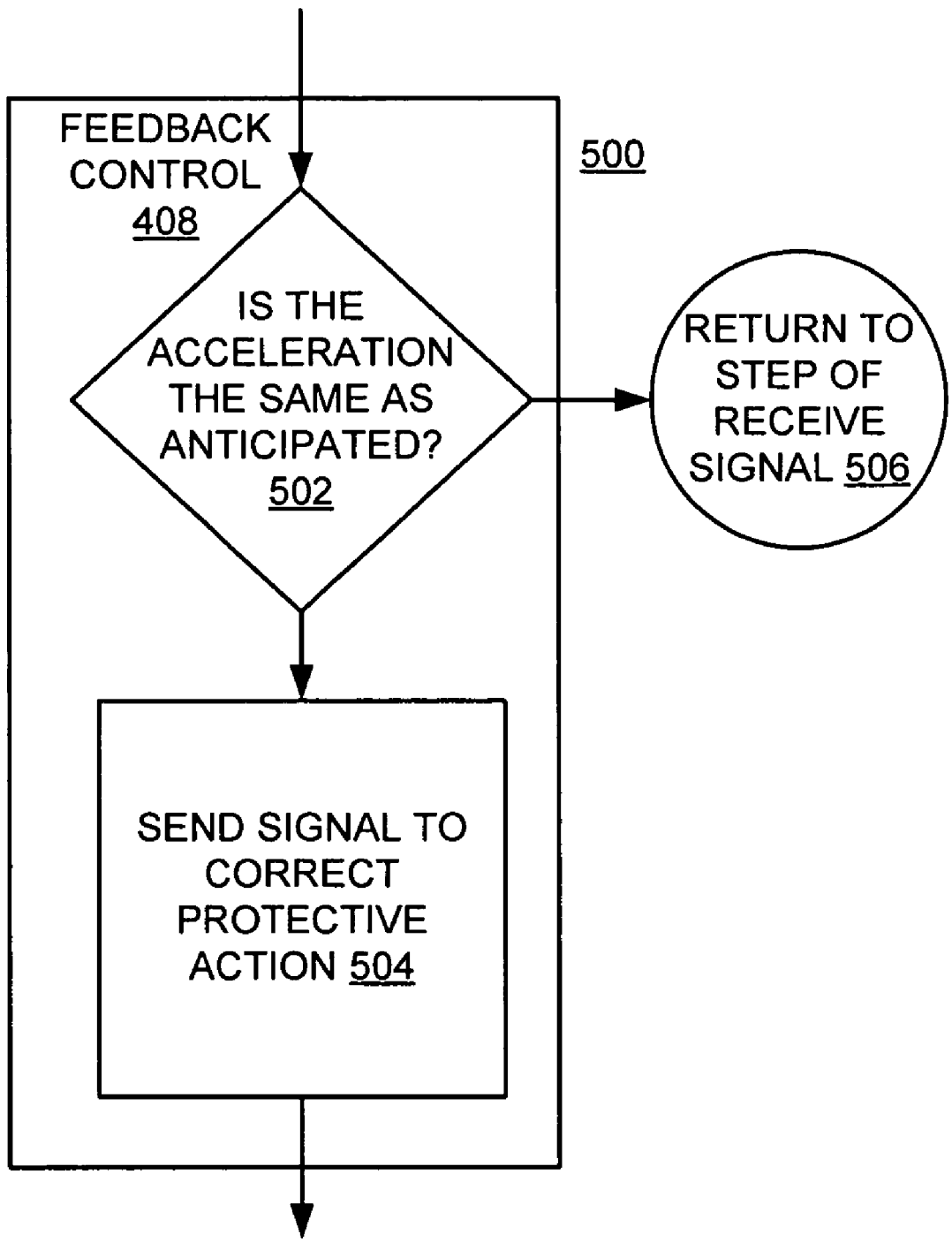
FIG. 5 depicts a flowchart of an example of a method that is an embodiment of a sub-step of the method of FIG. 4.

FIG. 5 depicts a flowchart of a method 500, which is an embodiment of sub-step 408. In sub-step 502, a determination is made whether the state (e.g., the movement or acceleration) of the object is the same as anticipated. If the state is not the same as anticipated, sub-step 502 proceeds to sub-step 504. In sub-step 504, a signal is sent to correct the protective action (that was previously activated) to accommodate for the deviation from the anticipated state. The accommodation for the deviation may be based on an updated expected state and/or upon updated measurements of kinematics of the body or at least one portion thereof and/or upon updated measurements of the object(s) with which an adverse interaction is projected. Returning to sub-step 502, if the state is the same as expected, then method 500 proceeds to sub-step 506.

In sub-step 506, method 500 returns to sub-step 210 (FIG. 2). In an embodiment, during step 506, method 500 continues to send signals to protective instrument 108 (FIG. 1A) that will continue the protective action that was previously activated, and may also receive signals back from 108. In other embodiments, the method 500 may include other sub-steps in addition to, and/or instead of, the steps listed above. Additionally, circuitry 106 (FIG. 1A) may perform the method 500 several times in response to different signals.

Figure 6:
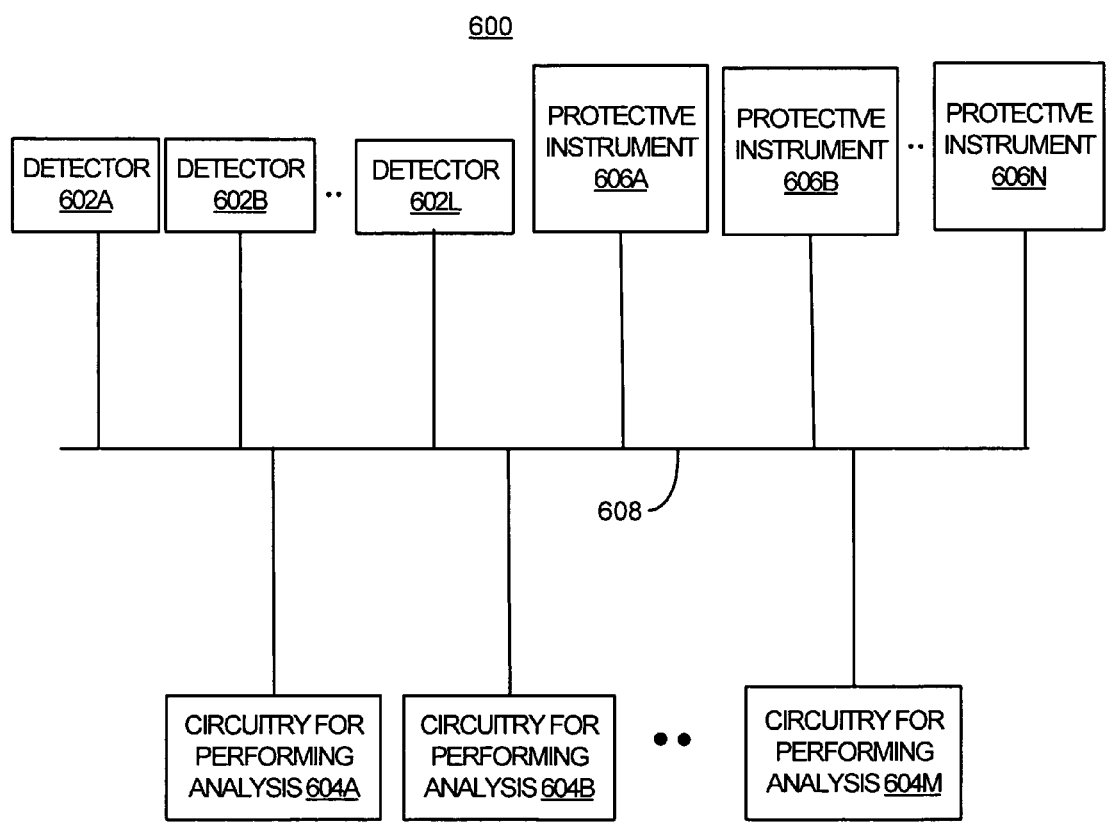
FIG. 6 depicts a block diagram of an embodiment of the system of FIG. 1 having multiple sensors, instances of circuitry, and protective instruments.

FIG. 6 depicts a block diagram of an alternative system 600 having multiple detectors, instances of circuitry, and protective instruments. System 600 includes detectors 602a-l, instances of circuitry 604a-m, protective instruments 606a-n, and communications link 608. In other alternative embodiments, system 600 may include other components in addition to and/or instead of those listed above.

System 600 is an embodiment of system 100 (FIG. 1A) that includes multiple detectors, instances of circuitry, and protective instruments. Detectors 602a-l may each be the same, or essentially the same, as sensor 102 (FIG. 1A). Similarly, instances of circuitry 604a-m may each be the same, or essentially the same, as circuitry 106 (FIG. 1A). Likewise, protective instruments 606a-n may each be the same, or essentially the same, as protective instrument 108 (FIG. 1A). The letters "l," "m," and "n," each represent any number. The values and relative values of letters "l," "m," and "n," are unrelated to one another. Each of letters "l," "m," and "n," may represent a number that is greater than, less than or equal to either or both of the numbers represented by the other two letters.

Detectors 602a-l may all be located within the vicinity of a single body or may be distributed amongst the vicinities of multiple bodies and/or objects. The number of detectors 602a-l that are distributed in the vicinity of each body and/or object may be unrelated to one another. In an embodiment, there may be only one of detectors 602a-l within the vicinity of each body. The number of detectors placed on a particular body may depend upon the size of the body, the tendency for the body to undergo adverse interactions, the degrees or severity of the adverse interactions anticipated to be possible and/or likely with the body, the characteristics of the body motion or that of one-or-more of its parts, and/or the places or types of environments that the body tends to be located or to traverse under various body-motion circumstances or conditions. The number of sensors placed on a particular body or any portion thereof may also depend on the circumstances-determined fragility of the body or portion thereof, the value or importance of the body and/or the number of available detectors, or other factors. In general and all other considerations being equal, the greater the number of detectors 602a-l that are located within the vicinity of a particular body or portion thereof, the more reliably, accurately, and precisely the state of the body or portion thereof may be estimated.

In an embodiment, detectors are placed only on the bodies and not on the objects (e.g., potentially-threatening objects). In another embodiment, detectors are also placed on some or all of these objects. Some objects may share one or more of detectors 602a-l. There may be any number of objects that all utilize the same one of detectors 602a-l, and any number of the objects sharing this detector may not be utilizing any other detector. The number of detectors 602a-l that are placed within the vicinity of a particular object may depend upon the number of available detectors 602a-l. The number of detectors 602a-l that are placed within the vicinity of a particular object may depend upon the value or fragility or other factors or considerations pertaining to the bodies expected to pass within the vicinity of the object. The number of detectors 602a-l that are placed within the vicinity of a particular object may depend on the nature or degree of adverse interaction that the body or portion thereof and/or the object are expected to sustain, should the body or portion thereof adversely interact with the object. The number of detectors placed within a vicinity of an object may depend upon the detailed circumstances of that vicinity. For example, there may be more detectors in the vicinities of objects that are located near corners, vicinities that have one or more changes in elevation, and/or vicinities that have changes in direction of a pathway or hallway than in straight hallways, in the particular case in which the adverse interaction may be inadvertent collisions of one-or-more portions of a (especially, locomotion-challenged) pedestrian's body with stationary objects.

Instances of circuitry 604a-m may operate independently of one another, or may form a distributed computational circuit and/or a distributed processor. Protective instruments 606a-n may be located on the same item deployed on-or-about a body or body-portion, or may be at distinct locations. Detectors 602a-l may measure at least two expected time-histories including at least one time-history for each of at least two portions of the body corresponding to each of protective instruments 606a-n.

Communications link 608 may be any means by which detectors 602a-l, instances of circuitry 604a-m, and protective instruments 606a-n may communicate with one another. For example, communications link 608 may be any combination of wires, optical fibers or other signal channels, and/or wireless links or other information-communicating means, e.g., acoustic links.

Figure 7:
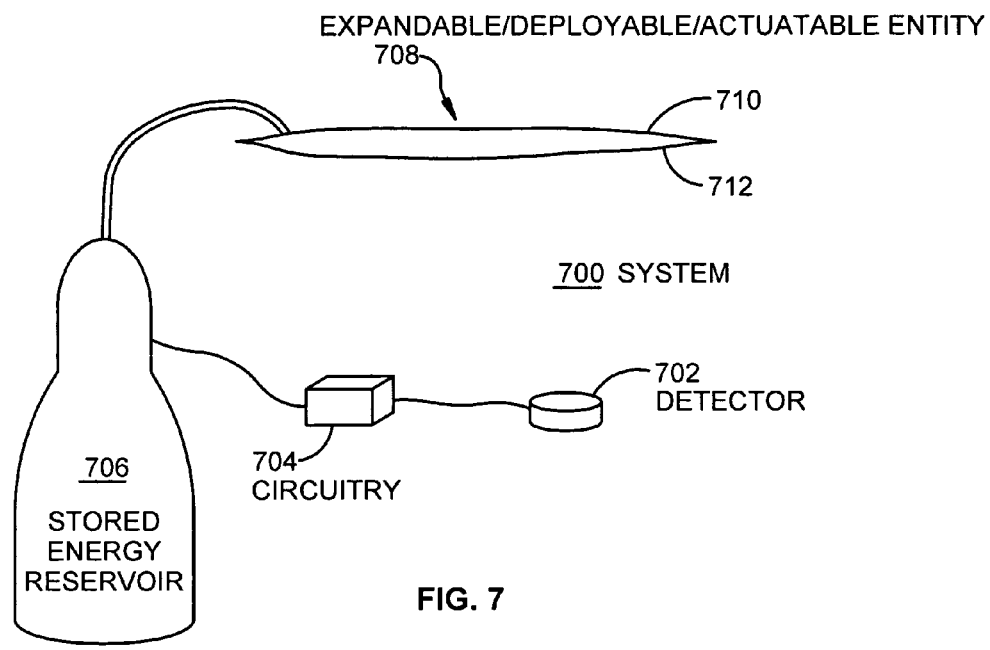
FIG. 7 depicts a system that is an example of one embodiment of the system of FIG. 1.

FIG. 7 depicts a system 700, which is one embodiment of system 100. System 700 includes detector 702, circuitry 704, stored energy reservoir 706, and expandable/deployable/actuatable entity 708 (e.g., a bag such as an air bag and/or a fluid-expandable entity such as might be expanded by one or more fluids such as and/or electrically heated and/or propelled fluids). Expandable/deployable/actuatable entity 708 may include components 710 and 712 (e.g., pieces of material) which may act to determine its size-&-shape and/or other salient feature when partly or fully expanded and/or otherwise actuated, e.g., as a result of introduction of pressurizing fluid from stored energy reservoir 706 and/or by one-time triggering actions (e.g., link-melting or connection-severing) commanded by circuitry 704. In alternative embodiments, system 700 may include other components in addition to and/or instead of those listed above.

Detector 702 is an embodiment of detector 104, and may function in the same manner as described above in conjunction with FIGS. 1-6. Circuitry 704 is an embodiment of circuitry 106, and may function in the same manner as described in FIGS. 1-6. Stored energy reservoir 706 and expandable/deployable/actuatable entity 708 form an embodiment of protective instrument 108 (FIG. 1A). Stored energy reservoir 706 may contain compressed gas or other pressurized fluid or some other source of high-pressure gas or liquid, or other forms of stored energy useful for actuating expandable/deployable/actuatable entity 708. Expandable/deployable/actuatable entity 708 is just one example of a type of structure for diffusing one or more impulses in spacetime that may be included in protective instrument 108. Similarly, expandable/deployable/actuatable entity 708 is just one example of an actuated device or structure that may be included in protective instrument 108. In response to receiving an appropriate signal from circuitry 704, stored energy reservoir 706 may generate and/or release pressurized gas and/or other fluid and/or other stored energy-forms, which begins to operate expandable/deployable/actuatable entity 708 which in turn is designed to modulate favorably an adverse interaction between the body or portion thereof and at least one object. In some implementations, stored energy reservoir 706 may be referred to as a source of an "impulse-diffusing agent," because, in response to being activated, stored energy reservoir 706 is at least partially involved in causing a cushioning effect to occur, in space, in time and/or in both.

Expandable/deployable/actuatable entity 708 may be formed in many possible fashions, e.g., by bonding pieces of material 710 and 712 to one another at their respective edges and/or by interconnecting other components or portions, with some of these interconnections possibly being capable of actuation themselves. The pertinent components of the entity 708 are designed and assembled so as to interact with the stored energy medium from reservoir 706 in such a manner to accomplish the adverse interaction-modulating function of entity 708, e.g., by adequately-swift inflation of a set of possibly-interconnected (and possibly nested and/or reentrant) gas-actuated compartments possibly constrained in their motions by internal connections also possibly controlled by circuitry 704, each perhaps to a particular protective situation-appropriate degree.

Each of detector 702, circuitry 704, energy reservoir 706, and expandable/deployable/actuatable entity 708 may be located on a position of a body so as to favorably modulate the 'baseline' adverse interaction between the body and/or portion thereof and the object. In one embodiment, the expandable/deployable/actuatable entity 708 is a thin gas-filled bladder that inflates so as to provide a protective cushioning layer of a few cm thickness between the object and the portion of the body which the object otherwise would contact, thereby diffusing in both space and time the stress which would otherwise result from the interaction—and thus reducing the peak stress that occurs anywhere at any time. Although only one detector 702, circuitry 704, stored energy reservoir 706 and expandable/deployable/actuatable entity 708 are shown, there may be any number of detectors, instances of circuitry, stored energy reservoirs, and expandable/deployable/actuatable entities. Detector 702, circuitry 704, stored energy reservoir 706 and expandable/deployable/actuatable entity 708 shown may represent one or more detectors, instances of circuitry, stored energy reservoirs, and expandable/deployable/actuatable entities, respectively. Each expandable/deployable/actuatable entity 708 may be individually controlled and individually actuated. In one embodiment, each expandable/deployable/actuatable entity 708 may contain a plurality of individually controlled and individually-actuated compartments, as well as any number of both passive and actuated fixtures, dimensional constraints and shape-determining and position-controlling devices emplaced within and between compartments.

Figure 8:
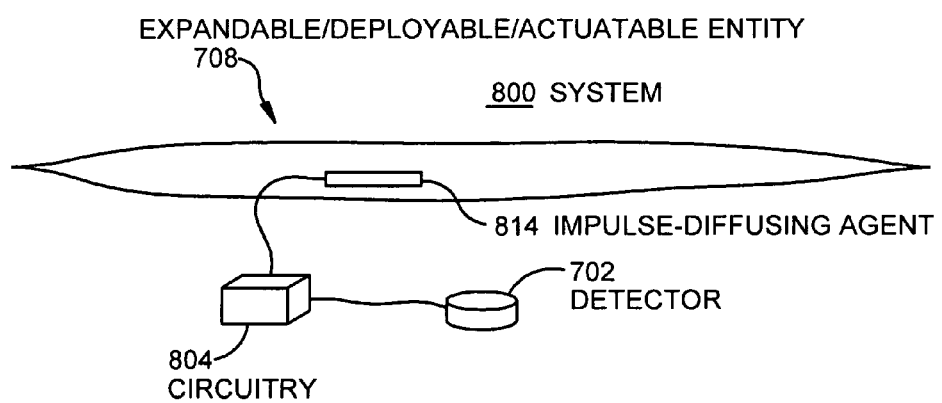
FIG. 8 depicts a system that is an example of another embodiment of the system of FIG. 1.

FIG. 8 depicts a system 800, which is another embodiment of the system 100. System 800 includes detector 702, expandable/deployable/actuatable entity 708, and circuitry 804. System 800 also includes impulse-diffusing agent 814. In alternative embodiments, system 800 may include other components in addition to and/or instead of those listed above.

Detector 702 and expandable/deployable/actuatable entity 708 are described in conjunction with FIG. 7. Circuitry 804 is an embodiment of circuitry 106 (FIG. 1A), and may function in a similar manner as described in FIGS. 1-6. Circuitry 804 may differ from circuitry 704 in that circuitry 704 may send signals that are appropriate for releasing pressurizing agent from stored energy reservoir 706, while circuitry 804 sends signals appropriate for activating an impulse-diffusing agent 814, which is not necessarily a stored energy reservoir but which may instead entail an energy conversion device and/or system.

Impulse-diffusing agent 814 is sometimes a device or material that, in response to receiving an appropriate signal from circuitry 804, causes expandable/deployable/actuatable entity 708 to be actuated. Impulse-diffusing agent 814 may release a gas or other elastic medium, device, or structure as a result of a chemical reaction caused by an electric current or voltage being applied by, or as a result of, signals from circuitry 804. In one embodiment, the impulse-diffusing agent 814 may be an azide material, such as sodium azide. In another embodiment, impulse-diffusing agent 814 causes a chemical reaction to occur that releases gas in a time-interval small compared to that upon which the adverse interaction would occur if it were not to be favorably modulated. Although only one detector 702, circuitry 804, expandable/deployable/actuatable entity 708, and impulse-diffusing agent 814 are shown, there may be any number of detectors, instances of circuitry, impulse-diffusing agents, and expandable/deployable/actuatable entities. Detector 702, circuitry 804, expandable/deployable/actuatable entity 708, and impulse-diffusing agent 814 may represent one or more detectors, instances of circuitry, impulse-diffusing agents, and expandable/deployable/actuatable entities, respectively.

Figure 9:
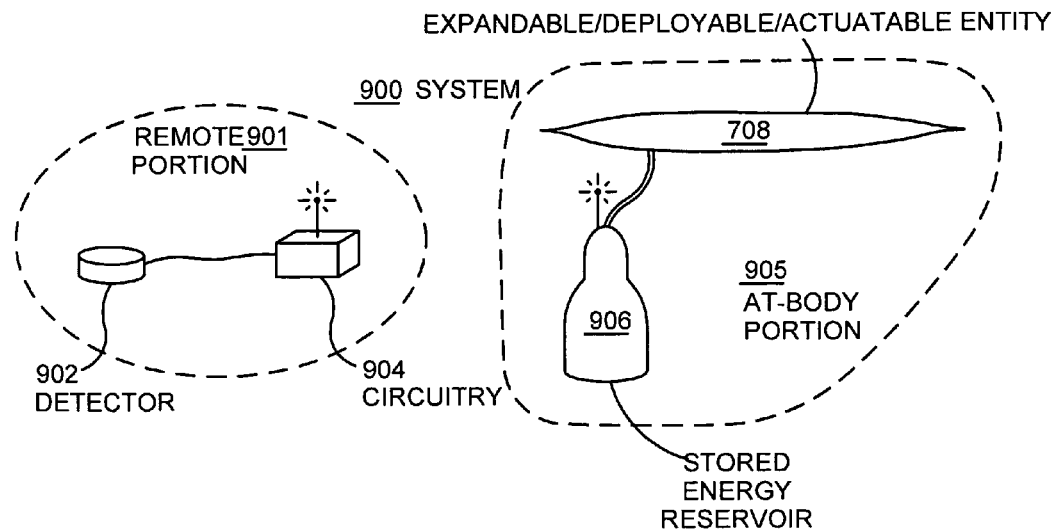
FIG. 9 depicts a system that is an example of another embodiment of the system of FIG. 1.

FIG. 9 depicts a system 900, which is another embodiment of the system 100 (FIG. 1A). System 900 includes remote portion 901, which has detector 902 and circuitry 904. System 900 also includes at-body portion 905, which has stored energy reservoir 906 and expandable/deployable/actuatable entity 708. In alternative embodiments, system 900 may include other components in addition to and/or instead of those listed above.

Expandable/deployable/actuatable entity 708 is described in conjunction with FIG. 7. Remote portion 901 is located remote from the body. For example, remote portion 901 may be located in a nexus that the body often traverses and/or near an object that would be damaging to the body were the body to interact adversely with the object. There may be several remote portions 901 located throughout a locality, such as a building or a vehicle. Alternatively, remote portion 901 may be located on-or-about the body, but remote from protective instrument 708. In an embodiment including multiple remote portions, there may be one or more remote portions located remote from the body and one or more remote portions 901 located on the body.

Detector 902 is an embodiment of detector 104 (FIG. 1A) and corresponds to detector 702 (FIG. 7). Detector 902 may function in a manner similar to that described above in conjunction with FIGS. 1-7. However, since detector 902 may be located at a remote location from the body, the manner in which detector 902 is configured may be somewhat different than the manner in which detector 702 is configured. Circuitry 904 is an embodiment of circuitry 106 (FIG. 1A) and corresponds to circuitry 704 (FIG. 7). Circuitry 904 may function in a manner similar to circuitry 106, instances of circuitry 604a-m, and/or circuitry 704 described in FIGS. 1-7. However, the analysis performed by circuitry 904 may be somewhat different from that of circuitry 704, because the signals received from detector 902 may represent a different perspective than the signal received from detector 702. Additionally, circuitry 904 is depicted as sending its signals (e.g., radio waves, light signals, and/or acoustic signals) via a wireless link to at-body portion 905, whereas circuitry 704 sends its signals via wire or optical fiber connection to the protective instrument. At-body portion 905 is an embodiment of protective instrument 108 (FIG. 1A), which is located on-or-about a body that is being protected to a degree from an object. Stored energy reservoir 906 corresponds to, and functions in a similar manner as, pressurized fluid reservoir 706 (FIG. 7), e.g., releasing gas causing expandable/deployable/actuatable entity 708 to actuate. However, stored energy reservoir 906 receives signals from circuitry 904, via a wireless link, whereas pressurized fluid reservoir 706 receives signals via a wire or optical fiber from circuitry 704.

Although only one remote portion 901, detector 902, circuitry 904, at-body portion 905, stored energy reservoir 906, and expandable/deployable/actuatable entity 708 are shown, there may be any number of remote portions, at-body portions, detectors, instances of circuitry, impulse-diffusing agents, and expandable/deployable/actuatable entities in system 900. Remote portion 901, detector 902, circuitry 904, at-body portion 905, stored energy reservoir 906, and expandable/deployable/actuatable entity 708 may represent one or more remote portions, detectors, instances of circuitry, at-body portions, stored energy reservoirs, and expandable/deployable/actuatable entities, respectively.

Figure 10:
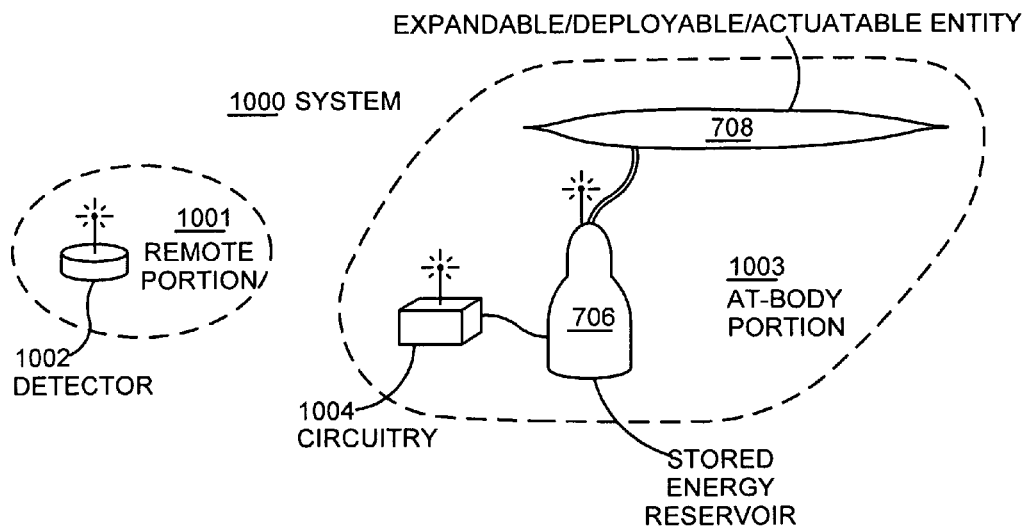
FIG. 10 depicts a system that is an example of another embodiment of the system of FIG. 1.

FIG. 10 depicts a system 1000, which is another embodiment of the system 100 (FIG. 1A). System 1000 includes remote portion 1001, which has detector 1002. System 1000 also includes at-body portion 1003, which has circuitry 1004, stored energy reservoir 706, and expandable/deployable/actuatable entity 708. In alternative embodiments, system 1000 may include other components in addition to and/or instead of those listed above.

Expandable/deployable/actuatable entity 708 is described in conjunction with FIG. 7. At-body portion 905 and stored energy reservoir 906 are described in conjunction with FIG. 9. Remote portion 1103 is located remote from at-body portion 905 and remote portion 1001. Remote portion 1103 may be located on the body or remote from the body. Circuitry 1004 is an embodiment of circuitry 106 (FIG. 1A), and functions in a manner similar to circuitry 904 (FIG. 9). Remote portion 1001 may be located on the body, but remote from at-body portion 1003. In an embodiment including multiple remote portions, there may be one or more remote portions located remote from the body and one or more remote portions 1001 located on-or-about the body.

Detector 1002 is an embodiment of detector 104 (FIG. 1A). Detector 1002 corresponds to detector 902, and may function in a manner similar to that described above in conjunction with FIG. 9. However, detector 1002 sends its signals (e.g., radio waves, light signals, and/or acoustic signals) via a wireless link to at-body portion 1003, whereas detector 902 sends its signals via a wire or an optical fiber connection to circuitry 904. Circuitry 1004 corresponds to circuitry 106 or 704, and may function in a manner similar to that described in FIGS. 1-7. However, the analysis performed by circuitry 1004 may be similar to that performed by circuitry 904, because detectors 902 and 1002 are in remote portions 901 and 1001, respectively, and therefore sense the motion of the body with respect to the object from comparable perspectives.

Although only one remote portion 1001, detector 1002, at-body portion 1003, circuitry 1004, stored energy reservoir 706, and expandable/deployable/actuatable entity 708 are shown, there may be any number of remote portions, detectors at-body portions, instances of circuitry, stored energy reservoirs, and expandable/deployable/actuatable entities in system 1000. Remote portion 1001, detector 1002, at-body portion 1003, circuitry 1004, stored energy reservoir 706, and expandable/deployable/actuatable entity 708 may represent one or more remote portions, detectors at-body portions, instances of circuitry, stored energy reservoirs, and expandable/deployable/actuatable entities, respectively.

Figure 11:
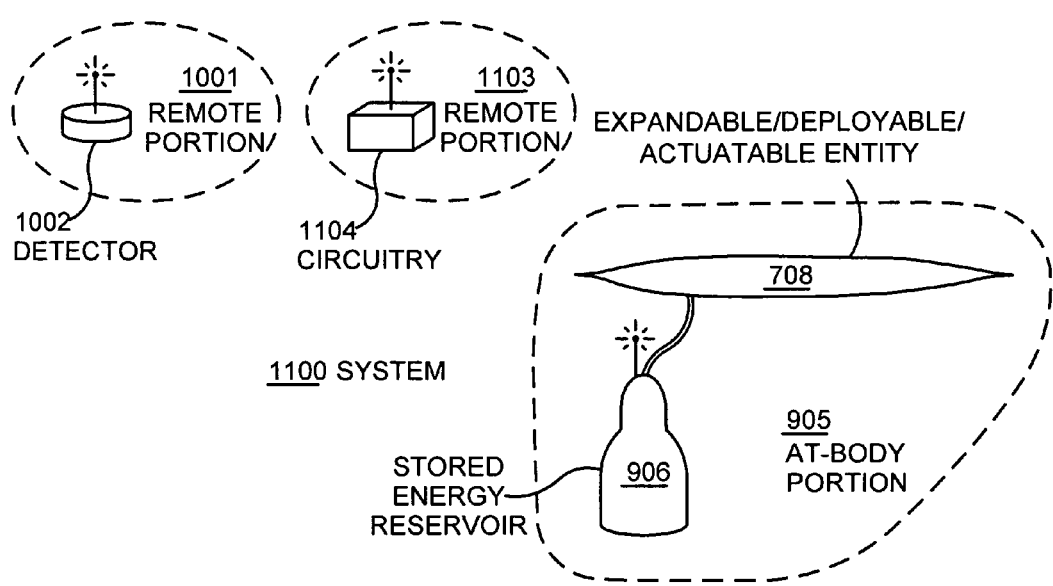
FIG. 11 depicts a system that is an example of another embodiment of the system of FIG. 1.

FIG. 11 depicts a system 1100, which is another embodiment of the system 100 (FIG. 1A). System 1100 includes remote portion 1001, which has detector 1002. System 1100 also includes remote portion 1103, which includes circuitry 1104. Further system 1100 includes at-body portion 905, which has stored energy reservoir 906 and expandable/deployable/actuatable entity 708. In alternative embodiments, system 1100 may include other components in addition to and/or instead of those listed above.

Expandable/deployable/actuatable entity 708 is described in conjunction with FIG. 7. At-body portion 905 and stored energy reservoir 906 are explained in conjunction with FIG. 9. Remote portion 1001 and detector 1002 are described in conjunction with FIG. 10. Remote portion 1001 may be located on-or-about the body, but remote from at-body portion 1003.

Remote portion 1103 is located remote from remote portion 1001 and at-body portion 905. In an embodiment including multiple remote portions, there may be one or more remote portions 1103 located remote from the body and one or more remote portions 1103 located on-or-about the body. There may be one or more remote portions 1103 located remote from the body and one or more remote portions 1103 located on-or-about the body. Circuitry 1104 is an embodiment of circuitry 106, and may function in a manner similar to that described in conjunction with FIGS. 1-6. The analysis performed by circuitry 1104 is similar to that performed by circuitry 1004 (FIG. 10) or 904 (FIG. 9), because detector 902 and 1002 are in remote portions 901 and 1001, respectively, and therefore detect the motion of the body with respect to the object from comparable perspectives. However, in contrast to instances of circuitry 1004 (FIG. 10) and 904 (FIG. 9), circuitry 1104 communicates wirelessly with both detector 1002 and stored energy reservoir 906.

Although only one remote portion 1001, detector 1002, remote portion 1103, circuitry 1104, at-body portion 905, stored energy reservoir 906, and expandable/deployable/actuatable entity 708 are shown, there may be any number of remote portions, detectors, instances of circuitry, at-body portions, stored energy reservoirs, and expandable/deployable/actuatable entities in system 1100. Remote portion 1001, detector 1002, remote portion 1103, circuitry 1104, at-body portion 905, stored energy reservoir 906, and expandable/deployable/actuatable entity 708 may represent one or more remote portions (for the detectors), detectors, remote portions (for the instances of circuitry), instances of circuitry, at-body portions, stored energy reservoirs, and expandable/deployable/actuatable entities, respectively.

Figure 12A:
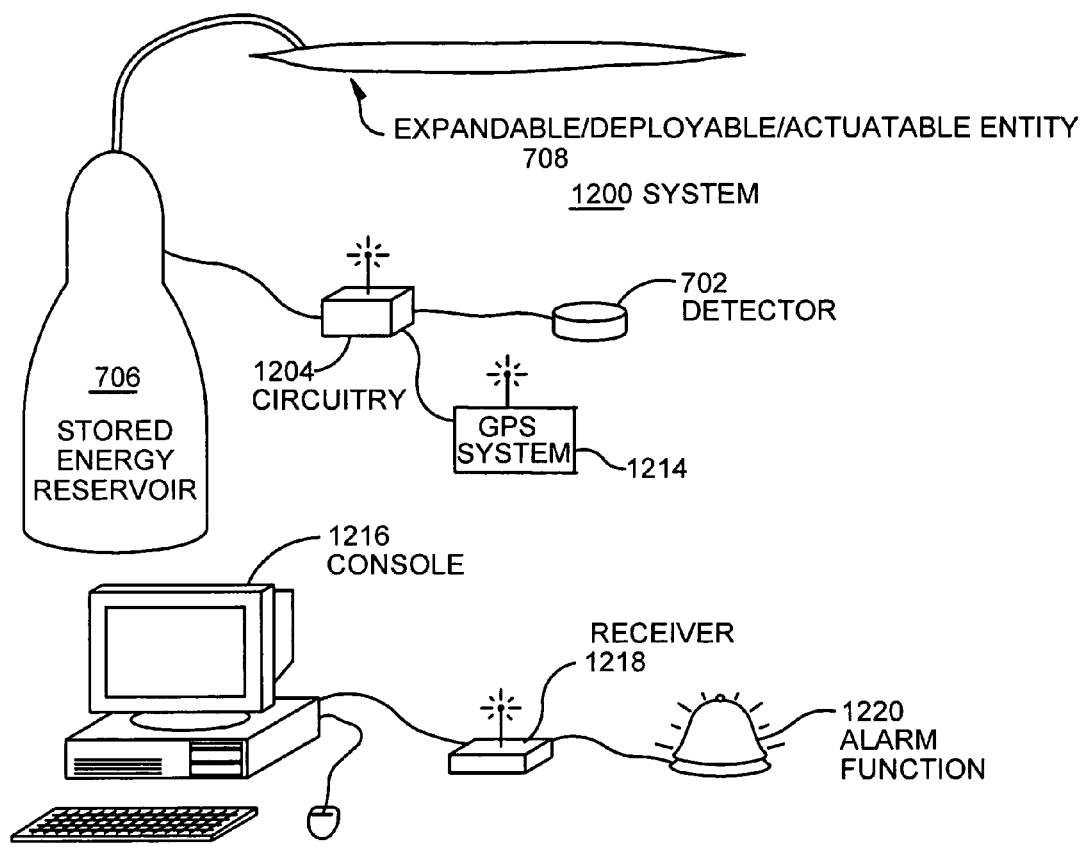
FIG. 12A depicts a system that is an example of another embodiment of the system of FIG. 1.

FIG. 12A depicts a system 1200, which is another embodiment of the system 100 (FIG. 1A). System 1200 includes detector 702, stored energy reservoir 706, and expandable/deployable/actuatable entity 708. System 1200 also includes circuitry 1204, Global Positioning System (GPS) 1214, console 1216, receiver 1218, and alarm function 1220. In alternative embodiments, system 1200 may include other components in addition to and/or instead of those listed above. (Throughout the present application, the term 'GPS' is typically used as a generic label to characterize any geolocation system of any type and employing any technology, whether conveying 'absolute' geodetic coordinates-&-time or analogous triangulation- or quadrangulation-enabling data (possibly not including any type of time-signal per se) referenced to some more local coordinate system.)

Detector 702, stored energy reservoir 706, and expandable/deployable/actuatable entity 708 are described in conjunction with FIG. 7. Circuitry 1204 is an embodiment of circuitry 106, and may function in a manner similar to that described in conjunction with FIGS. 1-6. Circuitry 1204 is also similar to circuitry 704 (FIG. 7). However, circuitry 1204 differs from circuitry 704 in that circuitry 1204 performs analysis of signals received from detector 702 to determine the state of the body after the adverse interaction with the object. The state of the body is analyzed to determine if the body has been adversely impacted beyond a particular degree that warrants sending a distress signal. Some examples of the body being adversely impacted to a degree that warrants sending a distress signal are if the body is immobilized, seriously injured, functionally broken, and/or cognitively disabled; for example, a likely broken hip or head injury resulting in dementia and/or loss of consciousness. For example, if the adversely-impacted body is a robot or a person, circuitry 1204 may use signals from detector 702 to determine whether or not the body is able to continue an adequate semblance of normal functioning. The degrees of adverse interaction required for activating the protective instrument and that required for sending a distress signal may be different.

Circuitry 1204 also differs from that of circuitry 704 (FIG. 7) in that circuitry 1204 may receive input from a GPS receiver, and may send a distress signal. GPS receiver 1214 is optional. GPS receiver 1214 may receive signals from satellites orbiting the earth that may be used to determine the location of the body having GPS receiver 1214, and/or its vector velocity and/or the absolute ('universal') time. Calculations may be performed by GPS 1214 receiver and/or circuitry 1204 that determine the position and/or vector velocity of the body based upon the signals received by GPS receiver 1214. Upon determining that the body has undergone an adverse interaction, circuitry 1204 may transmit information regarding the location of the body, the time of the adverse interaction, and/or other pertinent data. The information sent by circuitry 1204 may be based upon signals received from GPS receiver 1214. Circuitry 1204 may send a distress signal in addition to, or instead of, the location or time data. For example, in an embodiment not having GPS receiver 1214, circuitry 1204 may send a distress signal with little or no location information or with other location information derived from means different from that available from the GPS functionality.

Console 1216 is optional. Console 1216 may be a feature of a handheld computer, a laptop computer, a personal computer, a personal digital assistant, a computer-enabled personal communications device, a workstation, a mainframe computer, or a terminal, for example. Console 1216 may include one or more output devices, such as a monitor and/or a printer, which may be used to display or document information sent by, or derived from, the signals sent by circuitry 1204. Based on the information displayed or documented, an interested party may determine an appropriate action to take with respect to the body which has undergone the adverse interaction. The interested party may be a healthcare professional, a user, and/or a relative and/or an owner of the body, for example. Console 1216 may be associated with one-or-more databases that include information about multiple bodies, multiple locations, or other pertinent data. Console 1216 may perform diagnostic functions based on diagnostic and/or other information sent by circuit 1204. In an embodiment, circuitry 1204 may send status information about the body to console 1216 even when the body does not appear to have undergone an adverse interaction. The status information may include a descriptive assessment, location or position information, or information related to the direction of movement and/or information related to the speed of movement. The transmitted assessment may include estimates pertaining to the inferred state of the body and its recent history, particularly aspects of locomotion and environmental interactions. Console 1216 may also include a user interface for entering information, which information may be stored on machine-readable medium 112 (FIG. 1B).

Receiver 1218 receives signals from circuitry 1204 and transmits the signals to console 1216 and/or an alarm function 1220, which is optional. System 1200 may include none of, one of, or both of, console 1216 and alarm function 1220. Since both console 1216 and alarm function 1220 are optional, receiver 1218 is also optional. Specifically, receiver 1218 need not be included in system 1200 if console 1216 and alarm function 1220 are not present.

Alarm function 1220 receives signals from transmitter 1218 and alerts an interested party that there may be a problem with the body. Alarm function 1220 may include a bell, a beeper, a light source, a flashing light, a vibrator or any other device whose output can be sensed by a party bearing a component of alarm function 1220. In an embodiment, circuitry 1204 may include an alarm that sounds when circuitry 1204 determines that the body has undergone an adverse interaction with at least one object. A camera (not shown) may be associated with alarm function 1220, which turns on and shows the state of (e.g., images some fraction of) the body when it is detected that an adverse interaction has occurred. Upon detecting that an adverse interaction has occurred, an optical or acoustic (or other useful type of) signal at a station may be activated. The station may be monitoring the body and may be located at a hospital, home, school, and/or public-safety station, for example.

Although only one detector 702, stored energy reservoir 706, expandable/deployable/actuatable entity 708, circuitry 1204, GPS receiver 1214, console 1216, receiver 1218, and alarm function 1220 are shown, there may be any number of detectors, stored energy reservoirs, expandable/deployable/actuatable entities, instances of circuitry, GPS receivers, consoles, receivers, and alarm functions. Detector 702, stored energy reservoir 706, expandable/deployable/actuatable entity 708, circuitry 1204, GPS receiver 1214, console 1216, receiver 1218, and alarm function 1220 may represent one or more detectors, stored energy reservoirs, expandable/deployable/actuatable entities, instances of circuitry, GPS receivers, consoles, receivers, and alarm functions, respectively.

Figure 12B:
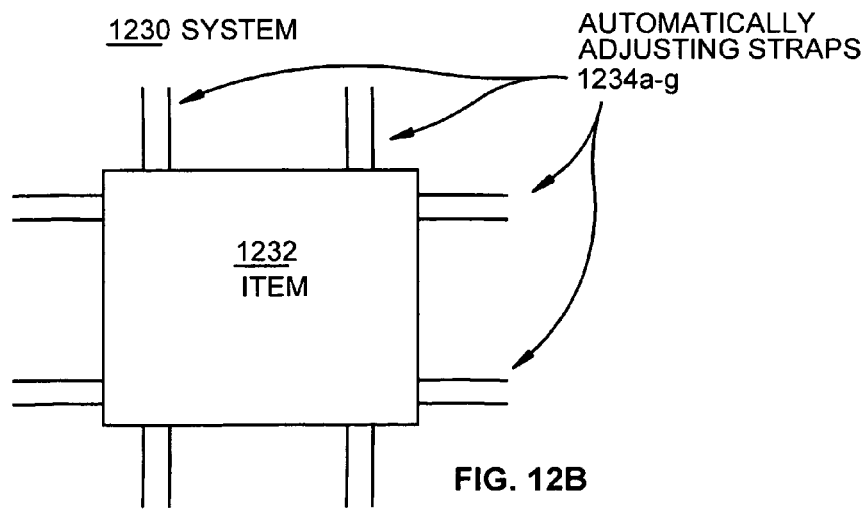
FIG. 12B depicts a system that is an example of an embodiment of the protective instrument of FIG. 1.

FIG. 12B depicts a system 1230, which is another embodiment of protective instrument 108 of FIG. 1. System 1230 includes item 1232 and straps 1234*a-g* (e.g., automatically adjusting straps). In alternative embodiments, system 1230 may include other components in addition to and/or instead of those listed above.

System 1230 depicts some possible mechanical means for affixing and/or adjusting the protective system on a body. Item 1232 may be a cushion or an expandable/deployable/actuatable entity such as expandable/deployable/actuatable entity 708 (FIGS. 7-12A), for example. In an embodiment, item 1232 may be positioned or oriented by straps or other means. Straps 1234*a-g* may be adjusted in response to signals from circuitry 106 (FIG. 1A) to position or orient or otherwise condition item 1232 so as to best protect a body or portion thereof against an projected adverse interaction and/or to allow item 1232 to actuate in a manner so as to favorably modulate an adverse interaction with one-or-more objects. Although in this embodiment there are 8 straps depicted in 1234*a-g*, in other embodiments there may be any number of straps or other different means of adjusting the position, orientation or actuation features or interaction-modulating capabilities of item 1232.

Although only one item 1232 and its set of straps are shown, there may be any number of items, each having a set of straps or other means for adjusting position, orientation, actuation features or interaction-modulation capabilities. Item 1232 and its set of straps may represent one or more functionally-similar items and their sets of adjustment means, respectively.

Regarding FIGS. 12C-25, any of the systems in FIGS. 1-12B may be included within many different types of items, such as garments or items-of-apparel or other devices or systems carried by or usually-&-reasonably closely associated with the particular type of body. FIGS. 12C-25 depict some non-exclusive examples of garments and other items within which the systems of FIGS. 1-12B may be included. More remarks applicable to FIGS. 12C-25 appear after FIG. 25.

Figure 12C:
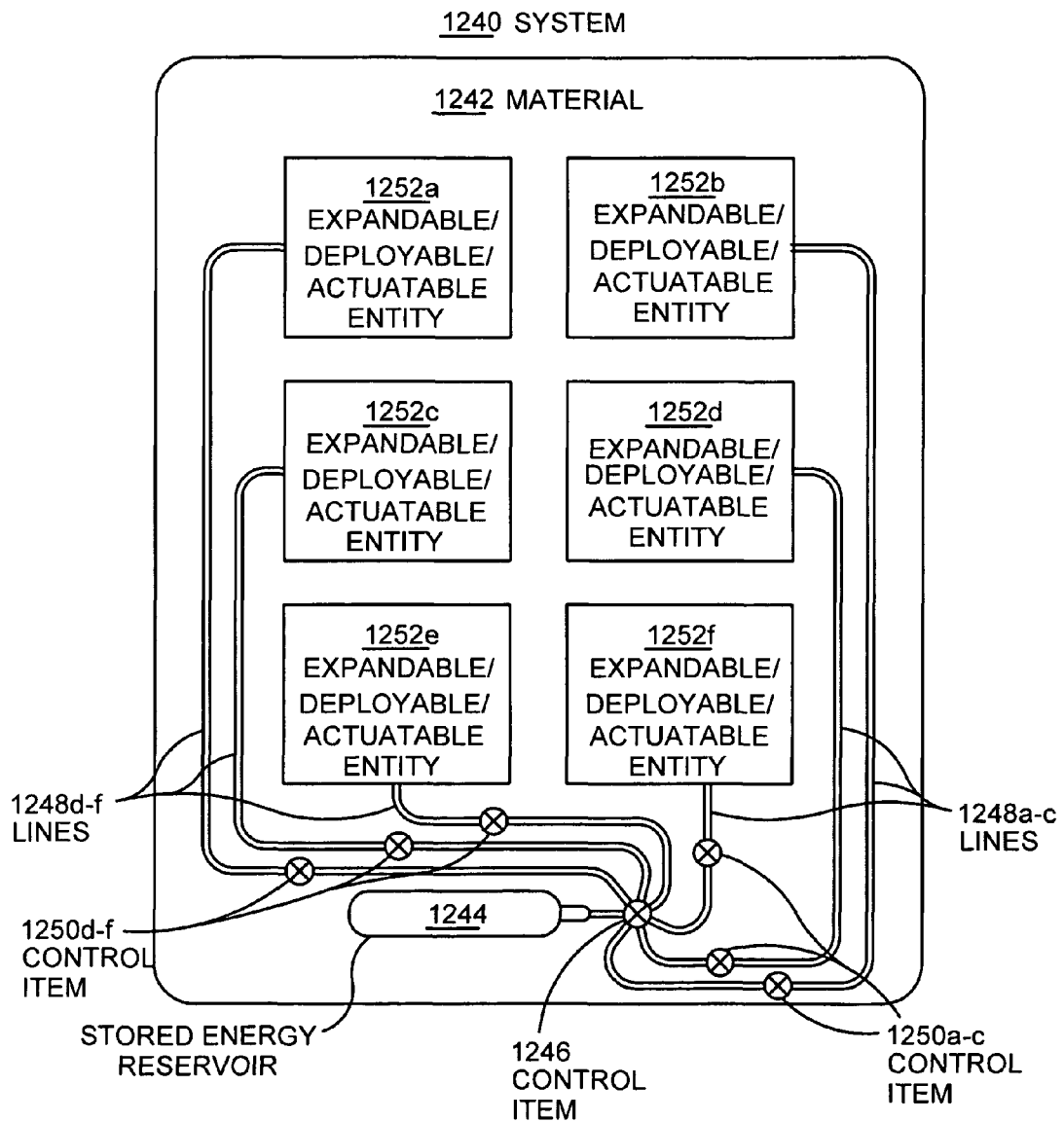
FIG. 12C depicts a system that is an example of an embodiment of the protective instrument of FIGS. 1, 6 and 7.

FIG. 12C depicts system 1240, which is an embodiment of the protective instruments of systems 100, 600, and 700 of FIGS. 1, 6, and 7, respectively. System 1240 includes material 1242, stored energy reservoir 1244, control item 1246 (an example of a more general control item), lines 1248*a-f*, valves 1250*a-f*, and expandable/deployable/actuatable entities 1252*a-f*. In alternative embodiments system 1240 may include other components in addition to and/or instead of those listed above.

Material 1242 is a material that is being worn by, or is a part of, the body being protected. For example, material 1242 may be part of a garment. Stored energy reservoir 1244 is an embodiment of stored energy reservoir 706. Control item 1246 controls the total flow of the pressurizing fluid out of stored energy reservoir 1244. Lines 1248*a-f* bring a stored-energy form from stored energy reservoir 1244 to corresponding expandable/deployable/actuatable entities 1250*a-f*. Control items 1250*a-f* control the flow of a stored-energy form, e.g., a pressurizing fluid, to each the corresponding expandable/deployable/actuatable entities. Control item 1246 is optional, because by controlling the individual flows using valves 1250*a-f* the aggregate flow may be controlled. Expandable/deployable/actuatable entities 1252*a-f* are more specific embodiments of expandable/deployable/actuatable entity 708. Each of expandable/deployable/actuatable entities 1252*a-f* may be constructed in the manner depicted for constructing expandable/deployable/actuatable entity 708 in FIG. 7. The amount or degree of expansion/deployment/actuation of each of expandable/deployable/actuatable entities 1252*a-f* is individually controlled. Each expandable/deployable/actuatable entity may be expanded or actuated to potentially a different degree according to a specification for modulating the adverse interaction. The modulation may take into account the various features of the body or major portion(s) thereof and of the one-or-more object with which the body may be adversely interacting, as well as the particular circumstances of the interaction.

Figure 12D:
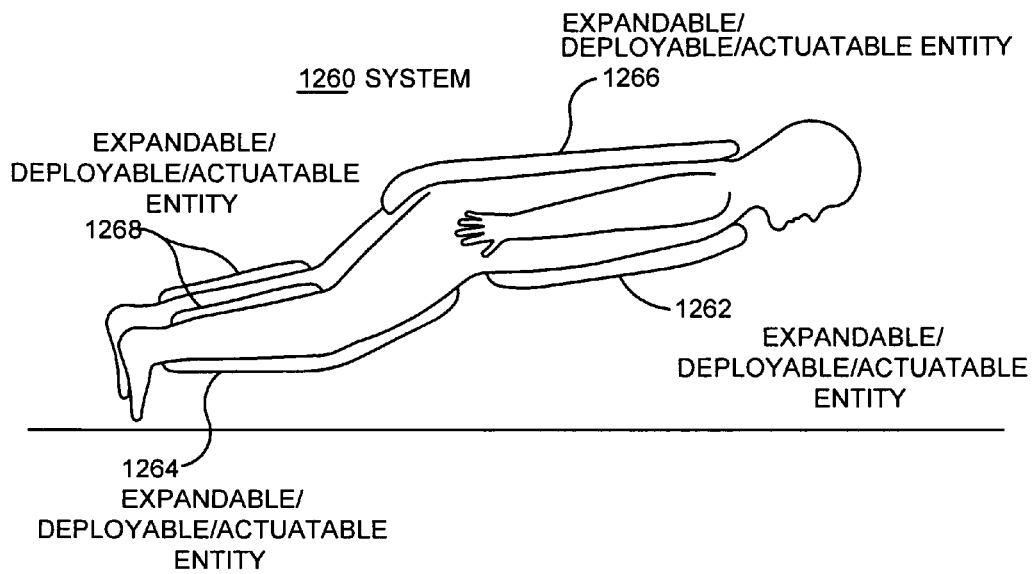
FIGS. 12D and 12E show a system, within which any combination of systems of FIGS. 1-12A may be used, in which different protective elements are activated, depending on how the body is accelerated and the nature of the potential adverse interaction with an object.
Figure 12E:
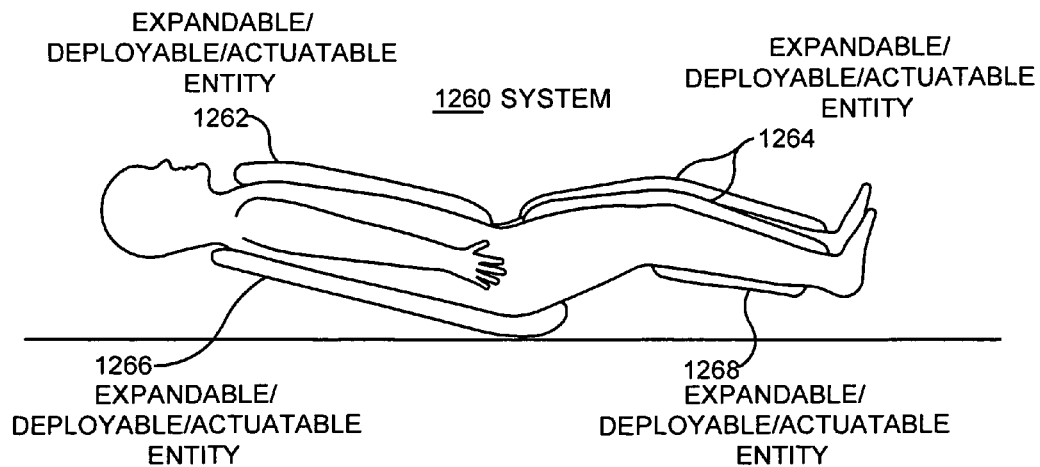

FIGS. 12D and 12E depict a system 1260 in which different expandable/deployable/actuatable entities are activated depending on how the body may be adversely interacting or projected to be adversely interacting with the one-or-more objects. System 1260 includes entities 1262, 1264, 1266, and 1268. In other embodiments, system 1260 may include other components in addition to or instead of those shown.

Each of expandable/deployable/actuatable entities 1262, 1264, 1266, and 1268 may include any of the systems described in conjunction with FIGS. 1-12A. Each of entities 1262, 1264, 1266, and 1268 may be a single entity with a single portion, or a single entity with multiple portions, each portion being capable of being separately activated to varying degrees. In FIG. 12D, the body fell forward, and consequently entities 1262 and 1264 were activated. In FIG. 12E, the body fell backwards and consequently entities 1266 and 1268 were activated. Which entities are activated and to what degrees is determined by the projected interaction with the one-or-more objects and an estimation of how to favorably modulate such interaction(s). In an embodiment, the responses of the two-or-more activated entities are coordinated to favorably modulate the net actions resulting from the responses. For example, if the head of a body is about to collide with an object, positioning an impulse-diffusing entity about the head may favorably modulate its interaction with the object, although so doing may also increase the likelihood of a neck injury as a result of the head being displaced a greater amount from the rest of the body than if the head-protecting action weren't taken. Consequently, in this embodiment, other entities may also be activated (e.g., about the neck and upper torso) in order to favorably modulate secondary consequences of the primary favorable modulation action(s). Those skilled in the art will appreciate that the expandable/deployable/actuatable entities of the figures herein are intended to be illustrative of many different types of entities; for example, the entities of FIG. 12D AND FIG. 12E may be considered representative of head and/or neck protective entities by straightforward logical extension.

Figure 13A:
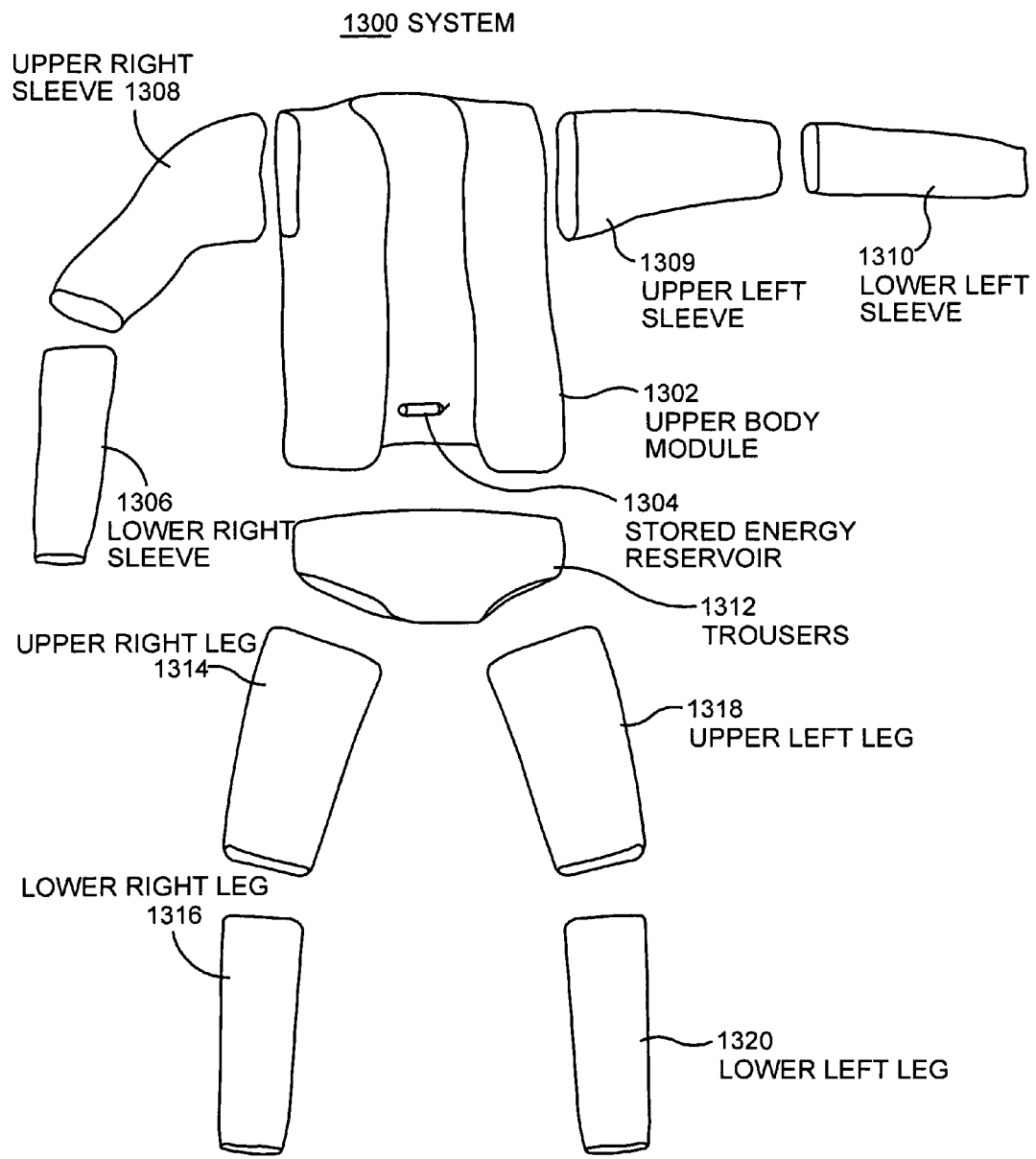
FIG. 13A depicts a system for protecting parts of a body, within which any combination of systems of FIGS. 1-12A may be used.

FIG. 13A depicts a system 1300 within which any combination of systems 100 and 600-1250 (described in conjunction with FIGS. 1-12A). System 1300 includes upper body module 1302 having stored energy reservoir 1304, lower right sleeve 1306, upper right sleeve 1308, upper left sleeve 1309, lower left sleeve 1310, trousers 1312, upper right leg 1314, lower right leg 1316, upper left leg 1318, and lower left leg 1320. In alternative embodiments system 1300 may include other components in addition to and/or instead of those listed above. As used herein, the term "module" is to be treated as more or less coextensive with the term "entity," unless context dictates otherwise.

System 1300 depicts a series of garments that may be worn as protective items without being visibly conspicuous. Upper body module 1302 is worn on-or-about, and protects, the chest of the body. Stored energy reservoir 1304 supplies a stored-energy form, e.g., a pressurized fluid to one or more expandable/deployable/actuatable modules within the upper body module 1302. Stored energy reservoir 1304 may be located in any convenient location, e.g., in-or-about a portion of upper body module 1302 that corresponds to the lumbar region of the body. Although stored energy reservoir 1304 is depicted as being oriented parallel to the bottom edge of upper body module 1302, reservoir 1304 may be positioned and/or oriented in any other fashion that may be convenient; it may consist of two or more physically distinct entities.

Each of the components of system 1300 protects the corresponding portion of the body. Lower right sleeve 1306 protects the lower right arm and may include the wrist. Upper right sleeve 1308 protects the upper part of the right arm and may include the elbow. Upper left sleeve 1309 protects the upper part of the left arm and may include the elbow. Lower left sleeve 1310 protects the left forearm and may include the wrist. Trousers 1312 protect the lower part of the trunk of the body. Upper right leg 1314 protects the upper part of the right leg and may include the knee. Lower right leg 1316 protects the lower part of the right leg and may include the ankle. Upper left leg 1318 protects the upper part of the left leg and may include the knee. Lower left leg 1320 protects the lower part of the left leg and may include the ankle. In some implementations, the various system components described herein are sized/shaped/arranged to give protective priority to the joints of the limbs and/or to the torso (e.g., ribs, spinal vertebrae) since such body components are viewed as mechanically weak points and likely to suffer damage.

Each of the components of system 1300 (upper body pad 1302 having stored energy reservoir 1304, lower right sleeve 1306, upper right sleeve 1308, upper left sleeve 1309, lower left sleeve 1310, pants 1312, upper right leg 1314, lower right leg 1316, upper left leg 1318, and lower left leg 1320) may have any number of stored energy reservoirs, expandable/deployable/actuatable entities, detectors, and/or instances of circuitry. For example, each of the components of system 1300 may include one or more of system 1250 (FIG. 12C). Alternatively, each of the components of system 1300 includes one expandable/deployable/actuatable module, for example. Each of the components of system 1300 may be worn as an undergarment, may be worn on top of normal clothing, and/or may be incorporated within or under or over other garments or other items-of-apparel, such as shirts and trousers, for example. Any of the components of system 1300 may be used to immobilize, restrain, stiffen, protectively cushion, and/or strengthen a body-limb and/or appendage. In an embodiment, any of the components of system 1300 may be used to protect, reduce or otherwise favorably modulate a break, such as skeletal bone-break, muscle, or other soft-tissue damage or other somatic structural failure or incapacity until more definitive or standardized treatment becomes available.

Figure 13B:
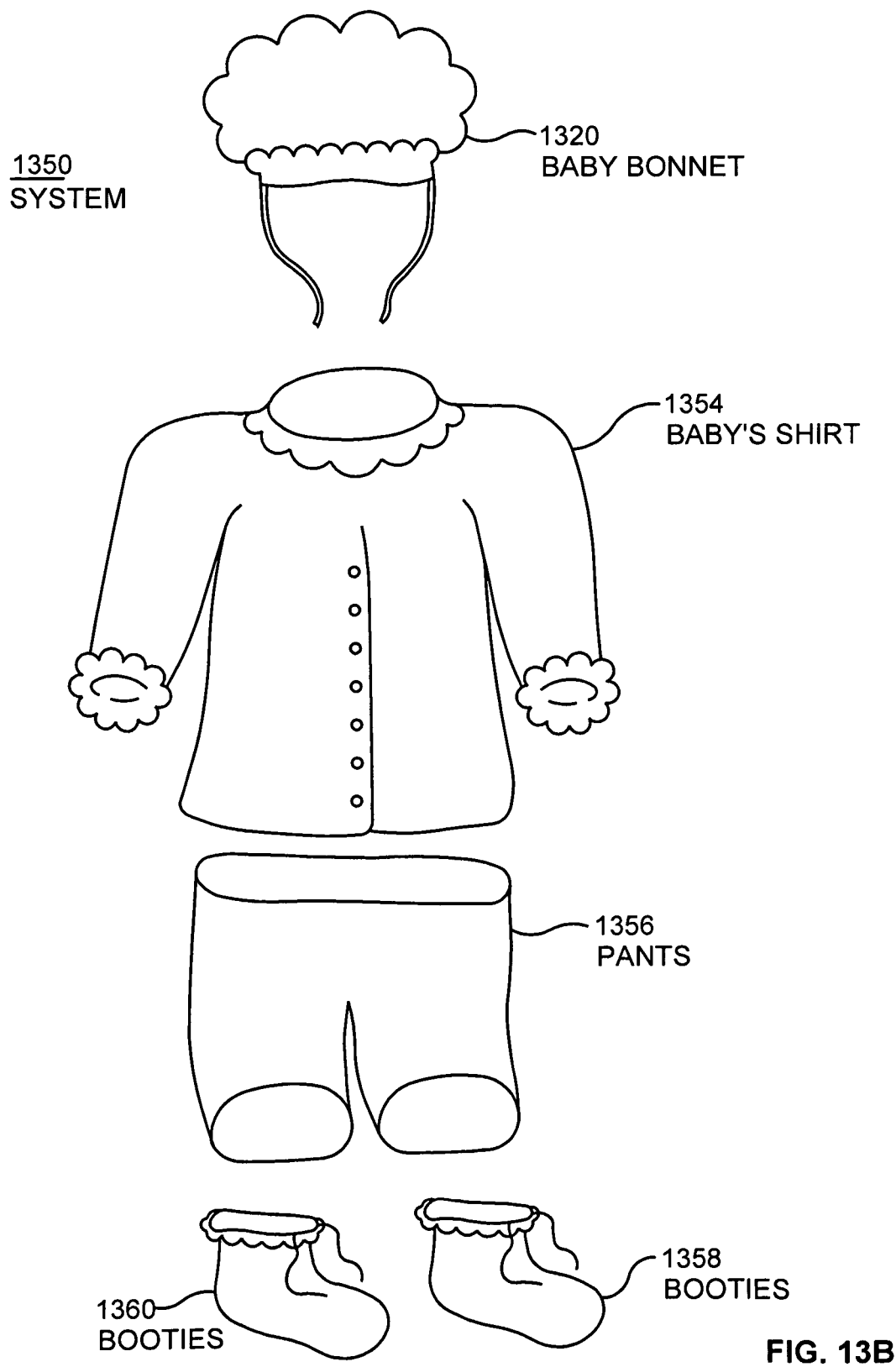
FIG. 13B shows a system for protecting the body of a baby within which any combination of systems of FIGS. 1-12A may be used.

FIG. 13B shows a system 1350 within which any combination of systems 100 and 600-1250 (described in conjunction with FIGS. 1-12A) may be deployed and/or utilized. System 1350, baby bonnet 1352, baby shirt 1354, baby pants 1356, and baby booties 1358 and 1360 are merely exemplary. In alternative embodiments, system 1350 may include other components in addition to and/or instead of those listed above.

Each of the components of system 1350 protects the corresponding portion of the body. Baby bonnet 1352 may include one or more protective instruments for protecting the baby's head and/or neck. The baby's shirt 1354 may include one or more protective instruments for protecting the baby's upper body and arms, as well as its neck-and/or head. Pants 1356 may include one or more protective instruments for protecting the lower body and the legs of the baby. Booties 1358 and 1360 may include one or more protective instruments for protecting the baby's feet; furthermore, those skilled in the art will recognize that the clothing items depicted are representative of other types of protective clothing, such as protective hand devices (e.g., gloves) and or protective footwear (e.g., boots) such as shown/described elsewhere herein. System 1350 differs from that of an adult, because babies tend to be less mobile and less concerned about their appearance.

FIG. 14 depicts a system 1400, which includes a shirt 1402 having an activatable collar 1404, which when actuated may protect a body or portion(s) thereof, e.g., portions of the head and/or neck. In other embodiments, system 1400 may include other components in addition to or instead of those listed. Incorporated within shirt 1402 or elsewhere on-or-about the body of the shirt-wearer may be one or more embodiments of system 100. One or more expandable/deployable/actuatable entities may cover selected regions of shirt 1402. Shirt 1402 includes collar 1404, which when actuated extends over the neck and portions of the head of the human body wearing system 1400. Actuatable collar 1404 also includes one or more protective instruments for protecting the neck and/or head of the body, and may deploy when activated up from the shoulders from a garment collar in a girdle-like mode. In an embodiment, collar 1404 may surround and cover the entire head, and may have internal surfaces that conform to the neck and/or the head so as to provide particular types of mechanical support and/or cushioning conducive to minimization of injury from pertinent types of adverse interactions.

FIG. 15A depicts a system 1500, which includes shirt 1502 and trousers 1504 for protecting a body from an adverse interaction with one-or-more objects. In other embodiments, system 1500 may include other components in addition to or instead of those listed. In some embodiments, shirt 1502 and trousers 1504 appear to be ordinary clothing and/or items-of-apparel, but include modules that are part of the protective instrument 108 embedded therein. An advantage of inconspicuously placing system 100 (FIG. 1A) (e.g., system 600, FIG. 6) within shirt 1502 and/or trousers 1504 (or within any other item that appears to be ordinary clothing) is that people may be more willing to wear garments including system 100 if system 100's presence is inconspicuous. For example, the system 100 may be sufficient thin and/or otherwise devoid of externally-distinguishing features as to be minimally-observable. However, in an embodiment, system 100 is conspicuous or noticeable, as more protective capabilities may be embedded within or about a garment, if the requirement of inconspicuousness is removed. In one embodiment, shirt 1502 and/or trousers 1504 may be water-washable and/or suitable for various modes of 'dry cleaning'.

Figures 16A, 16B:
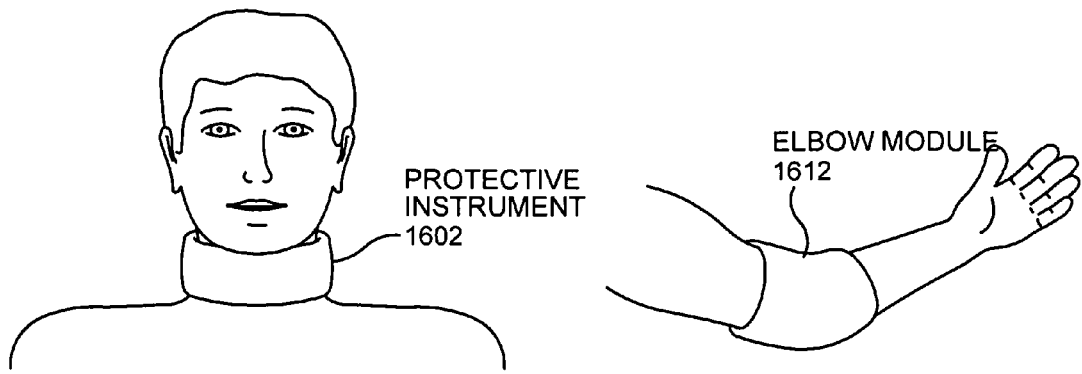
FIG. 16A depicts an example of a protective instrument for protecting a neck of a body, within which any combination of systems of FIGS. 1-12A may be used.
FIG. 16B depicts an example of a module for protecting an elbow of a body, within which any combination of systems of FIGS. 1-12A may be used.
Figures 17A, 17B:
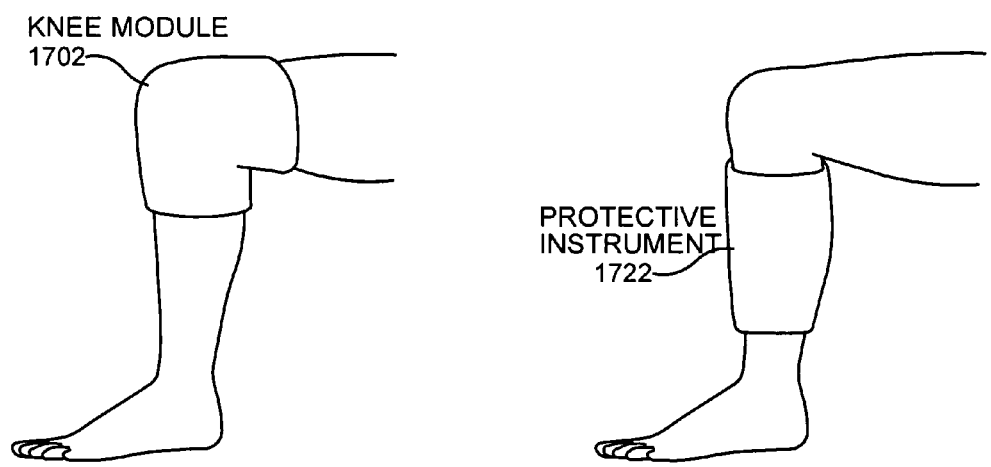
FIG. 17A depicts an example of a kneepad for protecting a knee of a body, within which any combination of systems of FIGS. 1-12A may be used.
FIG. 17B depicts a protective instrument for protecting a shin of a body, within which any combination of systems of FIGS. 1-12A may be used.
Figure 18:
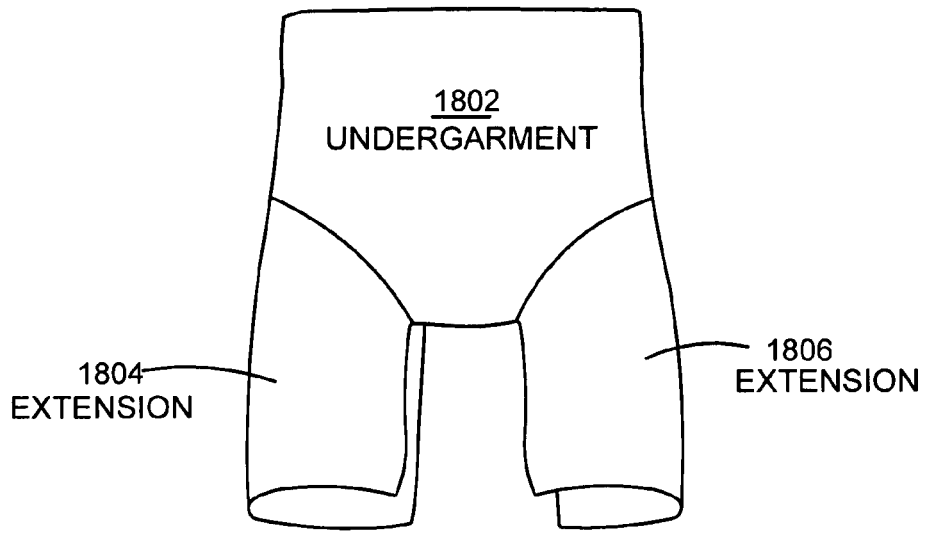
FIG. 18 depicts an undergarment having extensions for protecting a body, within which any combination of systems of FIGS. 1-12A may be used.
Figure 19A:
FIG. 19A depicts an example of a face mask, which may protect the nose and/or other parts of the head of a body, within which any combination of systems of FIGS. 1-12A may be used.
Figure 19B:
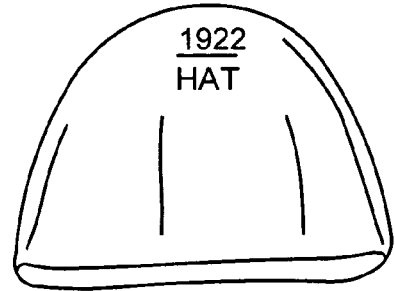
FIG. 19B depicts an example of a hat for protecting the head of a body, within which any combination of systems of FIGS. 1-12A may be used.

FIG. 15B depicts a jacket 1550 for protecting a body. In an embodiment, jacket 1550 is a ski jacket including modules that may protect a skier when the skier undergoes an adverse interaction with the immediate environment. FIG. 16A depicts a protective instrument 1602 for protecting from certain types of excessive transverse or rotational accelerations or excessive movements (e.g., such as might be associated with a neck, a wrist, an elbow, a knee, or an ankle). FIG. 16B depicts a module 1612 for protecting the elbow of a body from out-of-range motion or excessive transverse accelerations. FIG. 17A depicts a knee module 1702 for protecting a knee of a body from out-of-range motion or excessive transverse accelerations. FIG. 17B depicts protective instrument 1722 for protecting a shin of a body from excessive transverse accelerations or motions; quite similar devices would protect ankles and wrists from similar threats, and extensions thereof would perform likewise for hands and feet. FIG. 18 depicts a system 1800 having undergarment 1802 with extensions 1804 and 1806. The dotted lines separate the extensions from the rest of undergarment 1802. Extensions 1804 and 1806 partly cover, and are for protecting, the unusually-vulnerable upper thighs of a human body from excessive accelerations, e.g., ones resulting in femur-fracture proximate to the pelvic interface. Undergarment 1802 may likewise protect portions of the pelvis from excessive peak accelerations. FIG. 19A depicts a face mask 1902, which may protect the face and/or other parts of the head and/or neck from excessive peak accelerating forces. FIG. 19B depicts a hat or similar item of cranial apparel 1922 for protecting the skull of a human body from locally-excessive accelerations. In other embodiments, the systems of FIGS. 15B-19B may include other components in addition to or instead of those listed.

Figure 20:
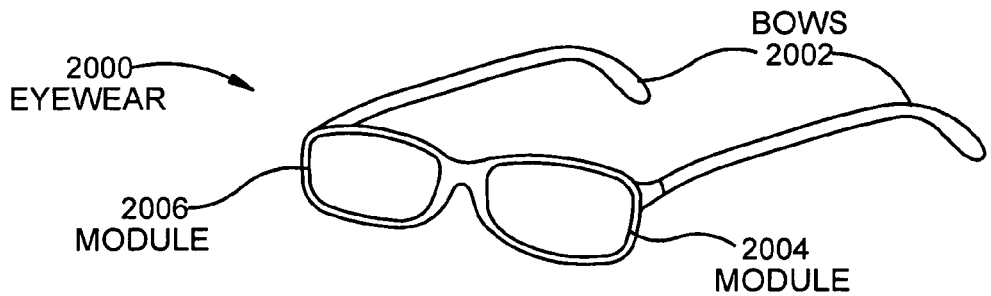
FIG. 20 depicts an example of eyewear having frames with pads, for protecting the eyes of a body, within which any combination of systems of FIGS. 1-12A may be used.

FIG. 20 depicts an example of eyewear 2000 having bows 2002 and modules 2004 and 2006. In other embodiments, system 2000 may include other components in addition to or instead of those listed. Eyewear 2000 could be any kind of glasses or goggles. For example, eyewear 2000 may be safety glasses, ski goggles, swimming goggles or goggles, e.g., ones that are intended to be worn while operating a vehicle that does not have a windshield. Bows 2002 support-&-position modules 2004 and 2006, and may be of any type. Modules 2004 and 2006 protect the eyes of a body. Each of modules 2004 and 2006 may include one or more expandable/deployable/actuatable entities that actuate to protect either or both of the eyes of the body from an adverse interaction. Modules 2004 and 2006 may actuate to enable cushioning action around the eyes, which modules may be incorporated into goggles 2000. Other modules may be placed elsewhere on frames or bows 2002 in addition to or instead of modules 2004 and 2006, e.g., to assist in maintaining the positioning of protective features during an adverse interaction.

Figure 21:
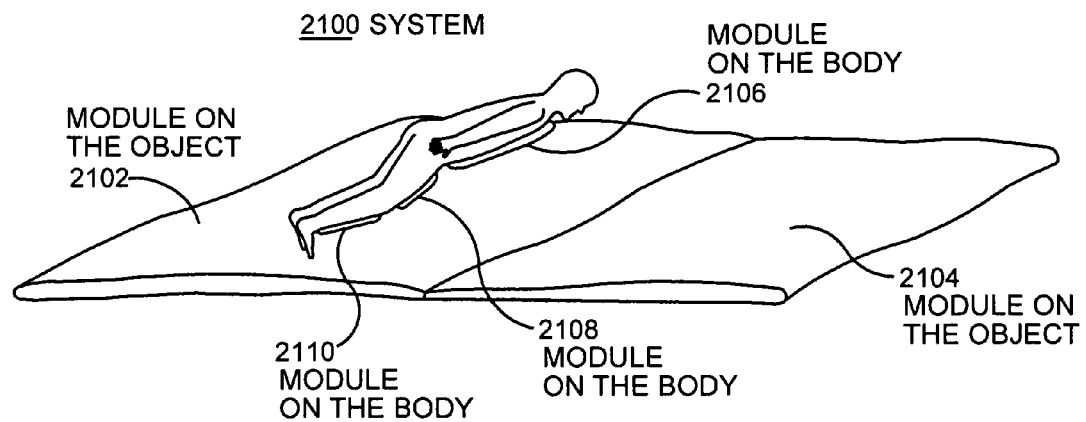
FIG. 21 depicts an example of a system that includes protective devices on both the body and the object, within which any combination of systems of FIGS. 1-12A may be used.

FIG. 21 depicts a system 2100, which includes actuatable modules on both the body and the potentially-threatening object. In other embodiments, system 2100 may include other components in addition to or instead of those listed. System 2100 includes modules 2102 and 2104 on the object and modules 2106, 2108, and 2110 on the body. The object on which the modules 2102 and 2104 are placed may be any object that may adversely interact with the body, e.g., objects and surfaces thereof in the body's immediate environment. Although only two large modules 2102 and 2104 are depicted, the modules may be any size and there may be any number of them. By placing modules on both the object and the body, there is brought into play a significantly richer set of options for modulating adverse interactions between body and object(s). Those skilled in the art will appreciate that the modules described herein are depicted as appropriately general so as to be structureable as appropriate to context. For example, in implementations where a certain body system(s) are to be protected, the modules shown are to be adapted to protect such systems. For instance, since it is contemplated that the hands and/or wrists might need protection, the modules herein, such as modules 2106, 2108, and/or 2110 are representative of hand-protective devices, such as gloves, as well as other body-system/component/member protective devices.

Figure 22:
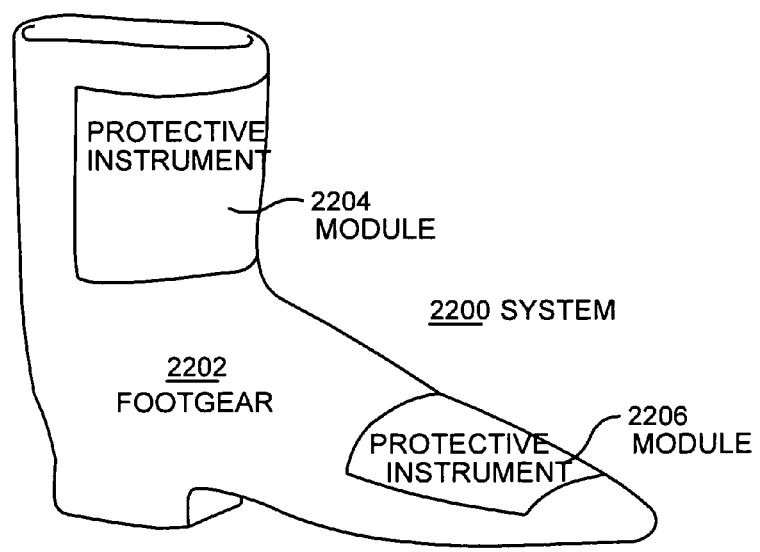
FIG. 22 depicts an example of system that includes footgear having protective devices within which any combination of systems of FIGS. 1-12A may be used.

FIG. 22 depicts system 2200, which includes footgear 2202 having modules 2204 and 2206. In other embodiments, system 2200 may include other components in addition to or instead of those listed. Footgear 2202 may afford protection against a variety of possible adverse interactions of the body or major portions with the body's environment and/or objects therein. In other embodiments, other modules may be included at other positions of footgear 2202 in addition to or instead of modules 2204 and 2206. Any of the embodiments of system 100 (FIG. 1A) (e.g., system 600, FIG. 6) may be used for modulating adverse interactions. System 2200 may also include at least one module for protecting the toes, e.g., from impacting objects.

Figure 23:
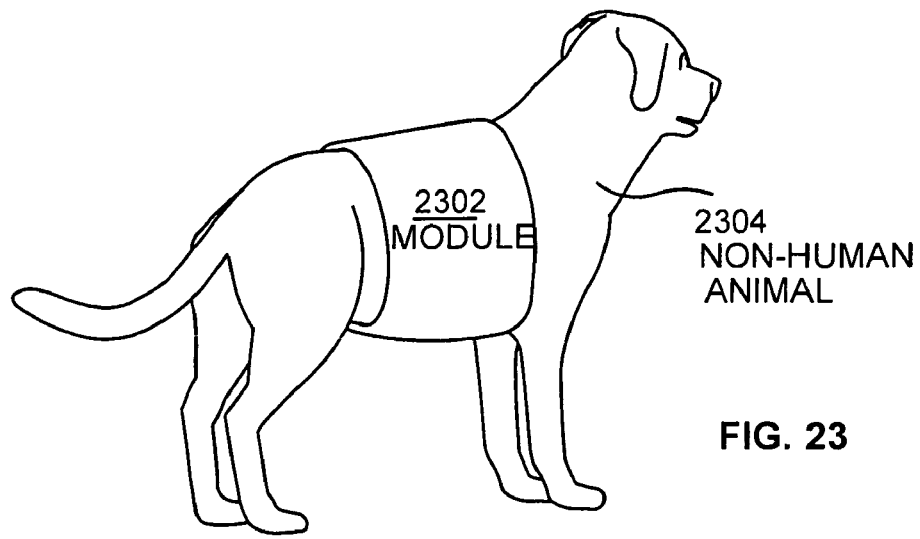
FIG. 23 depicts an example of a protective device for a body that is a non-human animal, within which any combination of systems of FIGS. 1-12A may be used.

FIG. 23 depicts a module 2302 for a body, which is a non-human animal 2304. Module 2302 may be located upon and used to protect other parts of the animal than that depicted, such as the head, the neck, the legs, ankles, and/or pelvis, etc.

Figure 24:
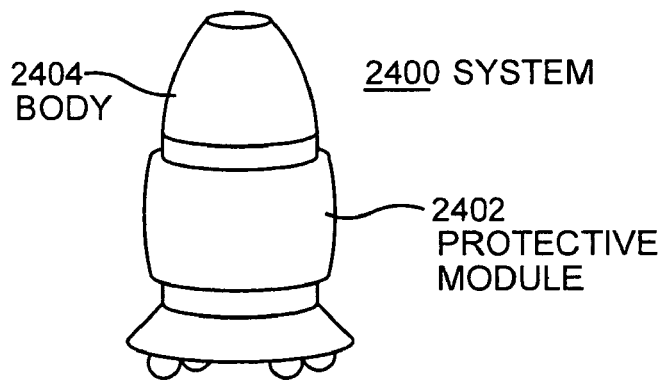
FIG. 24 depicts an example of a system having a protective device for a body, which is not living, within which any combination of systems of FIGS. 1-12A may be used.

FIG. 24 depicts a system 2400 having a protective module 2402 for a body 2404 that is not a living being. Body 2404 may be a robot, either stationary or mobile.

Figure 25:
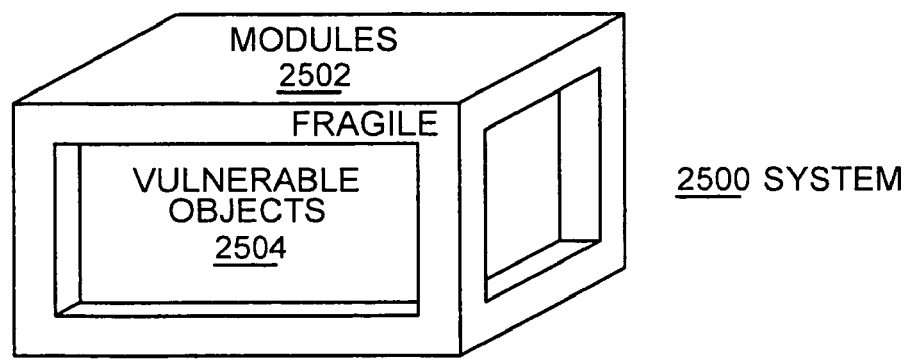
FIG. 25 depicts an example of a system having protective devices for a fragile object, within which any combination of systems of FIGS. 1-12A may be used.

FIG. 25 depicts a system 2500 having modules 2502 for a vulnerable object 2504. Modules 2502 protect vulnerable object 2504. In other embodiments, each of the systems associated with FIGS. 23-25 may include other components in addition to or instead of those listed.

Regarding FIGS. 15A-25, each of the garments or modules may include one or more modules that are capable of being activated, moreover each to various degrees and in various manners. Each of the modules may be capable of being individually activated, and each of its component parts likewise, moreover potentially to various degrees. Any of the modules may have multiple compartments or portions that are capable of being individually activated, moreover to various degrees or in various manners. The detectors and instances of circuitry used to activate the module(s) may be located on or about the body being protected and/or elsewhere. The protective devices of any of FIGS. 7-25 may include a deactivation function for deactivating which may be exercised to deactivate any the devices of FIGS. 15A-25, once their functioning is no longer desired. Alternatively, the protective devices of FIGS. 15A-25 could be removed or discarded after their functioning is no longer desired.

Although specific embodiments have been described, those skilled in the art will understand that various changes may be made and equivalents may be substituted for elements thereof without departing from the true spirit and scope of these embodiments. In addition, modifications may be made to the embodiments disclosed, without departing from the essential teachings herein.

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in standard integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies equally regardless of the particular type of signal bearing media used to actually carry out the distribution. Examples of a signal bearing media include, but are not limited to, the following: recordable type media such as floppy disks, hard disk drives, CD ROMs, digital tape, and computer memory; and transmission type media such as digital and analog communication links using TDM or IP based communication links (e.g., packet links).

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment).

Those skilled in the art will recognize that it is common within the art to describe devices and/or processes in the fashion set forth herein, and thereafter use standard engineering practices to integrate such described devices and/or processes into image processing systems. That is, at least a portion of the devices and/or processes described herein can be integrated into an image processing system via a reasonable amount of experimentation. Those having skill in the art will recognize that a typical image processing system generally includes one or more of a system unit housing, a video display device, a memory such as volatile and non-volatile memory, processors such as microprocessors and digital signal processors, computational entities such as operating systems, drivers, and applications programs, one or more interaction devices, such as a touch pad or screen, control systems including feedback loops and control motors (e.g., feedback for sensing lens position and/or velocity; control motors for moving/distorting lenses to give desired focuses. A typical image processing system may be implemented utilizing any suitable commercially available components, such as those typically found in digital still systems and/or digital motion systems.

Those skilled in the art will recognize that it is common within the art to describe devices and/or processes in the fashion set forth herein, and thereafter use standard engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

All of the above U.S. patents, U.S. patent application publications, U.S. patent applications, foreign patents, foreign patent applications and non-patent publications referred to in this specification and/or listed in any Application Data Sheet, are incorporated herein by reference, in their entireties.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of this subject matter described herein. Furthermore, it is to be understood that the invention is defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.).

What is claimed is:

1. A system comprising:
   means for sensing a particular state of a living body; and
   means for protecting the living body from an object responsive to the sensing, including
   means for determining one or more protective specifics related to at least one protective cushioning action located substantially at the body based upon accessing stored information associated substantially with an approximation of the living body's mass distribution, and
   means for activating the at least one protective cushioning action with the one or more protective specifics responsive to the means for determining.

2. The system of claim 1 wherein the means for sensing a particular state of a living body is located proximate to the body.

3. The system of claim 1 wherein the means for sensing a particular state of a living body is located remotely from the body.

4. The system of claim 1 wherein the means for sensing a particular state of a living body includes at least
   means for detecting motion; and
   means for determining whether the motion is likely to be the particular state.

5. The system of claim 1 wherein the means for sensing a particular state of a living body includes at least means for sensing an acceleration from substantially a beginning of a specified time-interval until substantially an end of the specified time-interval.

6. The system of claim 1 wherein the means for sensing a particular state of a living body includes at least means for sensing a direction of motion of the body.

7. The system of claim 1 wherein the means for sensing includes at least determining a location at which to perform the activating based on at least the direction of the sensed motion.

8. The system of claim 1 wherein the means for sensing includes at least means for sensing a vector direction of a motion.

9. The system of claim 1 wherein the means for sensing includes at least means for determining whether a positive indication of the particular state is substantially expected to be a false positive.

10. The system of claim 1 wherein
    the particular state is associated substantially with at least an acceleration of the body; and
    the means for sensing includes at least means for detecting motion; and
    means for determining whether the motion is likely to be substantially due to the acceleration.

11. The system of claim 1 wherein
    the particular state is associated substantially with at least an approximate positioning of the body; and
    the means for sensing includes at least means for determining the approximate positioning.

12. The system of claim 1 wherein the particular state is associated substantially with at least a change in an approximate positioning of the body; and
    the means for sensing includes at least means for determining the change in the approximate positioning.

13. The system of claim 1 wherein
    the particular state is associated substantially with at least an approximation of an acceleration of the body; and
    the means for sensing includes at least means for determining the approximation of the acceleration based on at least a time interval that is substantially shorter than a minimum time in which the body's center of mass is likely to move through a distance comparable to a distance between the body's center of mass and its lowest extremity.

14. The system of claim 1 wherein
    the particular state is associated substantially with at least an approximation of an acceleration of the body; and
    the means for sensing includes at least means for determining the acceleration based on at least a time interval that is expected to be sufficiently long to determine that an adverse interaction is likely to be imminent, and
    means for determining whether an adverse interaction is likely to be imminent.

15. The system of claim 1 wherein
    the particular state is associated substantially with at least an acceleration of the body; and
    the means for sensing includes at least means for determining the acceleration based on at least a time interval that is based on at least an approximate height of the body.

16. The system of claim 1 wherein the particular state is associated substantially with at least an acceleration of the body; and
    the means for sensing includes at least means for determining the acceleration based on at least a time interval, wherein the time interval is based substantially on at least a mass distribution associated substantially with at least the body.

17. The system of claim 1 wherein
    the particular state is associated substantially with at least an acceleration of the body; and
    the means for sensing includes at least means for determining the acceleration based on at least a time interval that is based substantially on at least an expected tensor that is based substantially on at least a size and/or shape of the body.

18. The system of claim 17, wherein the tensor is essentially independent of a value of mass associated substantially with at least the body.

19. The system of claim 17, wherein the tensor has a value that is substantially equal to a moment of inertia tensor associated substantially with at least the body divided by an estimated mass associated substantially with at least the body.

20. The system of claim 1 wherein the particular state is associated substantially with at least an expected contact with an object that is likely to be imminent, and
    the means for sensing includes at least means for determining whether the contact is likely to occur imminently.

21. The system of claim 1 wherein the particular state is associated substantially with at least an adverse interaction likely to be imminent, and
the means for sensing includes at least means for determining whether the adverse interaction is likely to occur imminently.

22. The system of claim 1 wherein
the particular state includes at least a deficiency of anticipated deceleration, and
the means for sensing includes at least means for determining whether the deceleration is substantially deficient relative to anticipation.

23. The system of claim 1 wherein the particular state includes at least the body being on a collision trajectory with the object, and
the means for sensing includes at least means for determining that the body is on an object-collision trajectory.

24. The system of claim 1 wherein the particular state includes at least
a deficiency of anticipated acceleration, and
the body being on a collision trajectory with the object; and
the means for sensing includes at least
means for determining whether the anticipated acceleration is substantially lacking, and
means for determining whether the body is substantially on a collision trajectory with the object.

25. The system of claim 1, wherein the at least one protective cushioning action is performed substantially at the body.

26. The system of claim 1, wherein the at least one protective cushioning action includes at least two protective actions that are substantially coordinated with one another in a manner based on an approximation of at least one of a size, a shape, or a known characteristic of the body and the state.

27. The system of claim 1, wherein the at least one protective cushioning action is substantially selected from a range of protective cushioning actions.

28. The system of claim 1, wherein the at least one protective cushioning action includes at least controlling an acceleration profile associated substantially with at least one or more parts of the body.

29. The system of claim 1, wherein the at least one protective cushioning action is based substantially on a feedback control of an acceleration.

30. The system of claim 1, wherein the protective cushioning action includes at least altering at least one of a position, an orientation, a size, or a shape of a protective element with respect to the body.

31. The system of claim 1, wherein the at least one protective cushioning action is not activated if the direction of the sensed motion is substantially upward.

32. The system of claim 1, wherein the at least one protective cushioning action includes at least forming a mechanically compliant protective region between the object and one or more proximate portions of the body.

33. The system of claim 1, wherein the at least one protective action includes at least forming a mechanically-rigid surface on or about a portion of the object which is proximate to at least one portion of the body.

34. The system of claim 1, wherein the at least one protective cushioning action includes at least generating and/or releasing a pressurized fluid including but not limited to a vapor and/or a gas, and
filling an expandable receptacle with the pressurized fluid.

35. The system of claim 34, wherein the generating and/or releasing of the pressurized fluid includes at least causing a chemical reaction that produces and/or releases the vapor and/or the gas.

36. The system of claim 34, wherein the generating and/or releasing of the pressurized fluid includes at least passing an electrical current through a material and thereby causing the vapor and/or the gas to be released by the material.

37. The system of claim 1, wherein the at least one protective cushioning action includes at least releasing a compressed vapor and/or gas into at least one expandable receptacle, thereby at least partly filling the at least one expandable receptacle with the vapor and/or gas released.

38. The system of claim 1, wherein the stored information associated substantially with an approximation of the body's mass distribution includes at least information related to approximations of the body's mass and inertial moments.

39. The system of claim 1, wherein the stored information associated substantially with an approximation of the body's mass distribution includes at least information related to at least one of the body's muscle distribution or the body's skeletal distribution.

40. A system comprising:
means for sensing a particular state of a body; and
means for, in response to a sensed particular state of a body, protecting the body from an object, including
means for determining one or more protective specifics related to at least one protective cushioning action based upon accessing stored information associated substantially with an approximation of the living body's mass distribution, and
means for activating the at least one protective cushioning action with the one or more protective specifics based on the determining.

41. A system comprising:
means for sensing via a sensor a particular state of a body; and in response to the sensing,
means for protecting a substantially living organism from an object, including
means for determining one or more protective specifics related to at least one protective cushioning action located substantially at the body based upon accessing at least some stored medical information associated substantially with at least one or more specifics of the substantially living organism; and
means for activating the at least one protective cushioning action with the one or more protective specifics based on the determining.

42. The system of claim 41, wherein the stored medical information associated substantially with at least one or more specifics of the substantially living organism includes at least a physical feature of an individual.

43. The system of claim 41, wherein the stored medical information associated substantially with at least one or more specifics of the substantially living organism includes at least medical damage information.

44. The system of claim 41, wherein the stored medical information associated substantially with at least one or more specifics of the substantially living organism includes at least vulnerability-related information.

45. A system comprising:
means for sensing a particular state of a body; and
means for, in response to a sensed particular state of a body, protecting a substantially living organism from an object, including means for determining one or more protective specifics related to at least one protective cushioning action located substantially at the body based upon accessing at least some stored medical information associated substantially with at least one or more specifics of the substantially living organism; and means for activating the at least one protective cushioning action with the one or more protective specifics based on the determining.

* * * * *